(12) United States Patent
Gordon et al.

(10) Patent No.: US 7,605,142 B2
(45) Date of Patent: Oct. 20, 2009

(54) EXPRESSION OF CYCLIN G1 IN TUMORS

(75) Inventors: Erlinda M. Gordon, Glendale, CA (US); Frederick L. Hall, Glendale, CA (US); W. French Anderson, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/553,416

(22) Filed: Oct. 26, 2006

(65) Prior Publication Data

US 2007/0172486 A1 Jul. 26, 2007

Related U.S. Application Data

(63) Continuation of application No. 10/218,542, filed on Aug. 14, 2002, now abandoned, which is a continuation of application No. 09/066,294, filed as application No. PCT/US96/17442 on Oct. 31, 1996, now abandoned, which is a continuation-in-part of application No. 08/551,486, filed on Nov. 1, 1995, now abandoned.

(51) Int. Cl.
C08B 11/193 (2006.01)

(52) U.S. Cl. ........................................................ 514/44
(58) Field of Classification Search .................... 514/44
See application file for complete search history.

(56) References Cited

U.S. PATENT DOCUMENTS

| | | | |
|---|---|---|---|
| 4,511,713 A | 4/1985 | Miller et al. | |
| 5,272,065 A | 12/1993 | Inouye et al. | |
| 5,449,755 A * | 9/1995 | Roberts et al. | 530/350 |
| 5,514,571 A | 5/1996 | Riabowol | |
| 5,543,291 A | 8/1996 | Keyomarsi et al. | |
| 5,710,022 A | 1/1998 | Zhu et al. | |
| 5,821,234 A | 10/1998 | Dzau | |
| 2002/0173538 A1 | 11/2002 | Shiao | |

FOREIGN PATENT DOCUMENTS

| | | |
|---|---|---|
| WO | WO 94/26888 | 11/1994 |
| WO | WO 02/18572 | 3/2002 |

OTHER PUBLICATIONS

Byers, T. (CA Journal, vol. 49, No. 6, Nov./Dec. 1999).*
Verma et al. (Nature 1997, 389: 239-242).*
Amalfitano et al. (Current Gene Therapy 2002, 2: 111-133).*
Pandha et al. (Current Opinion in Investigational Drugs 2000; 1(1): 122-134).*
McNeish et al (Gene Therapy, 2004, 11:497-503).*
McCormick (Nature Reviews, 2001, 1:130-141).*
Wu et al (Oncol Rep, 1994, 1:705-711).*
Griffin et al (J Biol Response Mod, Dec. 1988, 7(6):abstract).*
Verma et al. (Nature 1997, 389: 239-242).*
Amalfitano et al. (Current Gene Therapy 2002, 2: 111-133).*
Pandha et al. (Current Opinion in Investigational Drugs 2000; 1(1): 122-134).*
McNeish et al (Gene Therapy, 2004, 11:497-503).*
McCormick (Nature Reviews, 2001, 1:130-141).*
Wu et al (Oncol Rep, 1994, 1:705-711).*
Griffin et al (J Biol Response Mod, Dec. 1988, 7(6):559-567).*
Albers, et al. FKBP-Rapamycin inhibits a cyclin-dependent kinase activity and a cyclin D1-Cdk association in Early G1 of an osteosarcoma cell. J. Bio. Chem. 1993; 268(30):22825-22829.
Baker, et al. Suppression of human colorectal carcinoma cell growth by wild-type p53. Science. 1990; 249: 912-915.
Baldin, et al. Cyclin D1 is a nuclear protein required for cell cycle progression in G1. Genes Dev. 1993; 7(5):812-21.
Cohen, et al. The new genetic medicines. Scientific American. 1994; pp. 76-82.
Cripps, et al. Phase II randomized study of ISIS 3521 and ISIS 5132 in patients with locally advanced or metastatic colorectal cancer: a National Cancer Institute of Canada clinical trials group study. Clinical Cancer Research. 2002; 8:2188-2192.
Draetta, G. F. Mammalian G1 cyclins. Curr. Opin, In Cell Biol. 1994; 6:842-846.
Gentry et al. Type 1 transforming growth factor beta: amplified expression and secretion of mature and precursor polypeptides in Chinese hamster ovary cells. Mol. Cell. Biol. 1987: 7(10):3418-3427.
Gordon, et al. Induction of apoptosis by a human antisense cyclin G1 (CYCGI) gene in human osteogenic sarcoma cells after retroviral vector-mediated transfer. Blood. 1995; 86(Supp. 1):244a, Abstract 964.
Grim, et al. Intracellular expression of the anti-erbB-2 sFv N29 fails to accomplish efficient target modulation. Biochem. and Biophys. Res. Comm. 1998; 250:699-703.

(Continued)

*Primary Examiner*—Sean E Aeder
(74) *Attorney, Agent, or Firm*—Wilson Sonsini Goodrich & Rosati

(57) ABSTRACT

A method of treating a tumor (in particular osteosarcoma or Ewing's sarcoma) in a host by administering to a host or to the tumor cells an agent which inhibits cyclin G1 protein in an amount effective to inhibit cyclin G1 protein in tumor cells of the host. The agent may be an antisense polynucleotide which is complementary to at least a portion of a polynucleotide encoding cyclin G1 protein, or an antibody or fragment or derivative thereof which recognizes cyclin G1 protein. Also contemplated within the scope of the present invention are (i) the immortalization of cell lines by transducing cells with a polynucleotide encoding cyclin G1 protein; (ii) increasing the receptiveness of cells to retroviral infection by transducing cells with a polynucleotide encoding cyclin G1 protein; and (iii) the detection of cancer by detecting cyclin G1 protein or a polynucleotide encoding cyclin G1 protein in cells. In addition, the present invention provides expression vehicles, such as, for example, retroviral vectors and adenoviral vectors, which include polynucleotides which encode agents which inhibit cyclin G1 protein, and expression vehicles which include a polynucleotide encoding cyclin G1 protein.

7 Claims, 25 Drawing Sheets

OTHER PUBLICATIONS

Grinstein, et al. Multiple octamer-binding proteins are targets for the cell cycle-regulated nuclear inhibitor I-92. DNA and Cell Biol. 1995; 14(6):493-500.

Grunhaus, et al. Adenoviruses as cloning vectors. Seminars in Virology. 1992; 3:237-252.

Haprer, et al. Inhibition of cyclin-dependent kinases by p21. Mal Biol. Cell. 1995; 6:387-400.

Hartwell, et al. Cell cyclin control and cancer. Science. 1994; 266:1821-1828.

Horne, et al. Cyclin G1 and cyclin G2 comprise a new family of cyclins with contrasting tissue-specific and cell cycle-regulated expression. J. Biol. Chem. 1996; 271(11): 6050-6061.

Jones, et al. Antibodies for targeted gene therapy: extracellular gene targeting and intracellular expression. Advanced Drug Delivery Reviews. 1998; 31:153-170.

Majors, J. E. Retroviral vectors—strategies and applications. Seminars in Virology. 1992; 3:285-295.

Marshall, et al. A phase II trial of ISIS 3521 in patients with metastatic colorectal cancer. Clinical Colorectal Cancer. 2004; 4:268-274.

Okamoto, et al. Cyclin G is a transcriptional target of the p53 tumor suppressor protein. EMBO J. 1994; 13(19):4816-4822.

Oza, et al. Phase II study of CGP 69846A (ISIS 5132) in recurrent epithelial ovarian cancer: an NCIC clinical trials group study (NCIC IND.116). Gynecological Oncology. 2003; 89:129-133.

Skotzko, et al. Retroviral vector-mediated gene transfer of antisense cyclin G1 (CYCG1) inhibits proliferation of human osteogenic sarcoma cells. Cancer Research. 1995; 55:5493-5498.

Tamura, et al. Cyclin G: a new mammalian cyclin with homology to fission yeast Cig1. Oncogene. 1993; 8:2113-2118.

Tolcher, et al. A randomized phase II and pharmacokinetic study of the antisense oligonucleotides ISIS 3521 and ISIS 5132 in patients with hormone-refractory prostate cancer. Clinical Cancer Research. 2002; 8:2530-2535.

Williams, et al. Identification of a novel cyclin-like protein in human tumor cells. Journal of Biological Chemistry. 1993; 268:8871-8880.

Wu, et al. Early G1 induction of p21/WAF1/CIP1 in synchronized osteosarcoma cells is independent of p53. Oncology Reports. 1995; 2:227-231.

Wu, et al. Molecular cloning of the human CYCG1 gene encoding a G-type cyclin: overexpression in a human osteosarcoma cells. Oncology Reports. 1994; 1(4):705-711.

Wu, et al. Sequential and progressive cyclin expression in human osteosarcoma cells: Diagnostic and the therapeutic implications. Int. J. Oncology. 1993; 3:859-867.

Xiong, et al. Human D-type cyclin. Cell. 1991; 65:691-699.

Zhu, et al. Extended half-life and elevated steady-state level of a single-chain Fv intrabody are critical for specific intracellular retargeting of its antigen, caspase-7. J. Immune Methods. 1999; 231:207-222.

* cited by examiner

FIG. 1A

SEQ ID NO:1

```
    acaactgactctcagaaactgctacaccagctgaatgccctgttggaacaggagtctaga
1   ------+---------+---------+---------+---------+---------+  60 tgtcagccaaaggtctgtggtttgagactaattgagtctgcacacgataatggcctcaga
61  ------+---------+---------+---------+---------+---------+ 120 atgactgcaagactaagggactttgaagtaaaagatctcttagtctaactcagttcttt
121 ------+---------+---------+---------+---------+---------+ 180
    M  T  A  R  L  R  D  F  E  V  K  D  L  L  S  L  T  Q  F  F
```

SEQ ID NO:2

```
    ggctttgacacagagacatttctctagctgtgaattactggacagattcctgtctaaa
181 ------+---------+---------+---------+---------+---------+ 240
    G  F  D  T  E  T  F  S  L  A  V  N  L  L  D  R  F  L  S  K atgaaggtacagcccaagcaccttgggtgttggactgtgagctgctttattggctgta
241 ------+---------+---------+---------+---------+---------+ 300
    M  K  V  Q  P  K  H  L  G  C  V  G  L  S  C  F  Y  L  A  V aaatcaatagagagaggaaaggaatgtcccattggcaactgacttgatccgaataagtcaa
301 ------+---------+---------+---------+---------+---------+ 360
    K  S  I  E  E  E  R  N  V  P  L  A  T  D  L  I  R  I  S  Q tataggtttacggtttcagactttgatgagaatggaaaagattgtattggagaaggtgt
```

MATCH WITH FIG. 1B

FIG. 1B

MATCH WITH FIG. 1A

```
361 ---------+---------+---------+---------+---------+---------+ 420
     Y  R  F  T  V  S  D  L  M  R  M  E  K  I  V  L  E  K  V  C tggaaagtcaaagctactactgcctttcaatttctgcaactgtatattcactccttcaa
421 ---------+---------+---------+---------+---------+---------+ 480
     W  K  V  K  A  T  T  A  F  Q  F  L  Q  L  Y  Y  S  L  L  Q gagaacttgccacttgaaaggagaaatagcattaatttgaaagactagaagctcaactg
481 ---------+---------+---------+---------+---------+---------+ 540
     E  N  L  P  L  E  R  R  N  S  I  N  F  E  R  L  E  A  Q  L aaggcatgtcattgcaggatcatatatttctaaagcaaagccttctgtgttggcattgtct
541 ---------+---------+---------+---------+---------+---------+ 600
     K  A  C  H  C  R  I  I  F  S  K  A  K  P  S  V  L  A  L  S atcattgcattagagatccaagcacagaagtgtgtagagttaacagaaggaatagaatgt
601 ---------+---------+---------+---------+---------+---------+ 660
     I  I  A  L  E  I  Q  A  Q  K  C  V  E  L  T  E  G  I  E  C cttcagaaaacattccaagataaatggcagagatctgaccttctggcaagagcttgtatcc
661 ---------+---------+---------+---------+---------+---------+ 720
     L  Q  K  H  S  K  I  N  G  R  D  L  T  F  W  Q  E  L  V  S aaatgttaactgaatattcatcaaataagtgttccaaccaaatgttcagaagttgaaa
721 ---------+---------+---------+---------+---------+---------+ 780
     K  C  L  T  E  Y  S  S  N  K  C  S  K  P  N  V  Q  K  L  K
```

MATCH WITH FIG. 1C

FIG. 1C

MATCH WITH FIG. 1B

```
         tggattgtttctgggcgtactgcacggcaattgaagcatagctactacagaataactcac
781      ------+---------+---------+---------+---------+---------+ 840
         W  I  V  S  G  R  T  A  R  Q  L  K  H  S  Y  Y  R  I  T  H   240 cttccaacaattcctgaaatggtcccttaactggattattacagcaccaaaaaacttctc
841      ------+---------+---------+---------+---------+---------+ 900
         L  P  T  I  P  E  M  V  P                                   249 tgaagcctttctccacaaccttgttctatggattccataatgttacaatggatttaagct
901      ------+---------+---------+---------+---------+---------+ 960 atgaagcctcaaaacatcacgagataagcatgatggtctcagacttgggaaactgccta
961      ------+---------+---------+---------+---------+---------+ 1020 atattatgctgtagtggaattatgtttagatttgaattcatctgtgaagcattcaaagca
1021     ------+---------+---------+---------+---------+---------+ 1080 aagctaaaagcctaaatgtgaaatgctaatgacaagcctgagaaggtaaactgtgaatct
1081     ------+---------+---------+---------+---------+---------+ 1140 tcatttctatcattgatctaactttagatattggatcaatatattaggtggtattgaaa
1141     ------+---------+---------+---------+---------+---------+ 1200 atgctattggaggagtcacactaatactatcaactatcagtcttcccacagcttcaatca
1201     ------+---------+---------+---------+---------+---------+ 1260
```

MATCH WITH FIG. 1D

FIG. 1D

MATCH WITH FIG. 1C

```
1261 ctgtcattattctaatcctactcctacttaaatttaagttatgaggtttatgtcaaaag 1320
     ------+---------+---------+---------+---------+---------+

1321 caacatttcacaaatgtactttaaggcataataagggttaacattctaggcagtataaa 1380
     ------+---------+---------+---------+---------+---------+

1381 cacaccccataatgcaagtaataggtaatctagagatgtggactttattgctatatggga 1440
     ------+---------+---------+---------+---------+---------+

1441 attacatttaaatttgagggcatttatataagaaatacagacctataagttggcatattc 1500
     ------+---------+---------+---------+---------+---------+

1501 attaagttatctttaatattttttctagaaacaggtgacatttgatctatcgataaaattt 1560
     ------+---------+---------+---------+---------+---------+

1561 tatacagaacctactgcctcaaactgaatcccatcaagaaaactagtttctattgtatta 1620
     ------+---------+---------+---------+---------+---------+

1621 gtaactcaaaataaattatcacttcgaaaacttgctttcccactaaggtaagttcaga 1680
     ------+---------+---------+---------+---------+---------+

1681 ctagattgaacactccagaatttttactacagactgttttaagttagaagtgatggca 1740
     ------+---------+---------+---------+---------+---------+ atttataaatagagaatatacttccactgatgccctactgtgccaaacaaaatctt
```

MATCH WITH FIG. 1E

FIG. 1E

MATCH WITH FIG. 1D

```
1741 ------------------------------------------------------------ 1800
     ------------------------------------------------------------

1801 aagaaaagcaagtagacaccttcataactatgaatgaagctgctgaagtagtgtttagga 1860
     ------------------------------------------------------------

1861 tcctccatggcagttagtgaatgtaagagtacagtgttaagtgttgtaaacagttact 1920
     ------------------------------------------------------------

1921 cagtgcaatgtatagcctgagtctatccatgatggctatatccaattgacatcacgtta 1980
     ------------------------------------------------------------

1981 tggatcagtacacaatgaaaaaccaagaaccacgtatatcttattcttaactttgtaa 2040
     ------------------------------------------------------------

2041 accatgtttatgggtaacttttttagtttcccaaaggctgataaattcaatatttg 2100
     ------------------------------------------------------------

2101 aatacatcattgttaatttgagttggcagaggtaaactaaccaactaccattatgtttt 2160
     ------------------------------------------------------------

2161 agtactaagggatatacctttcaataagttaatgaaattcaaaaaaaaaaaaaaa 2219
     ------------------------------------------------------------
```

FIG. 2
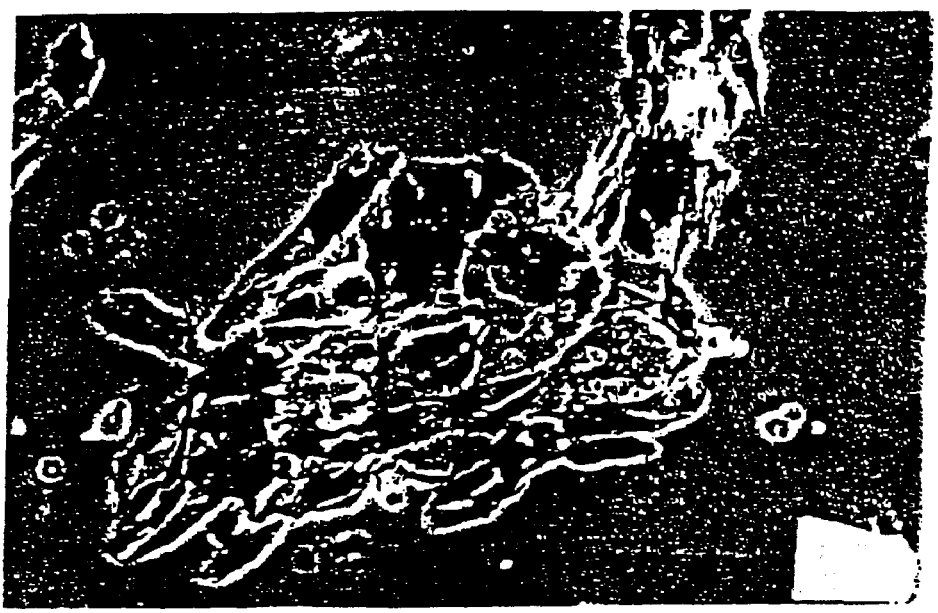
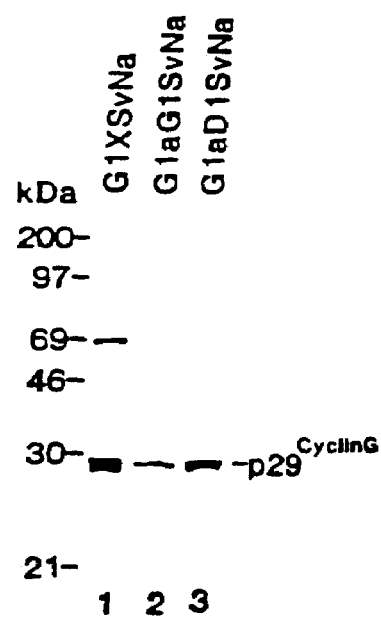
FIG. 6

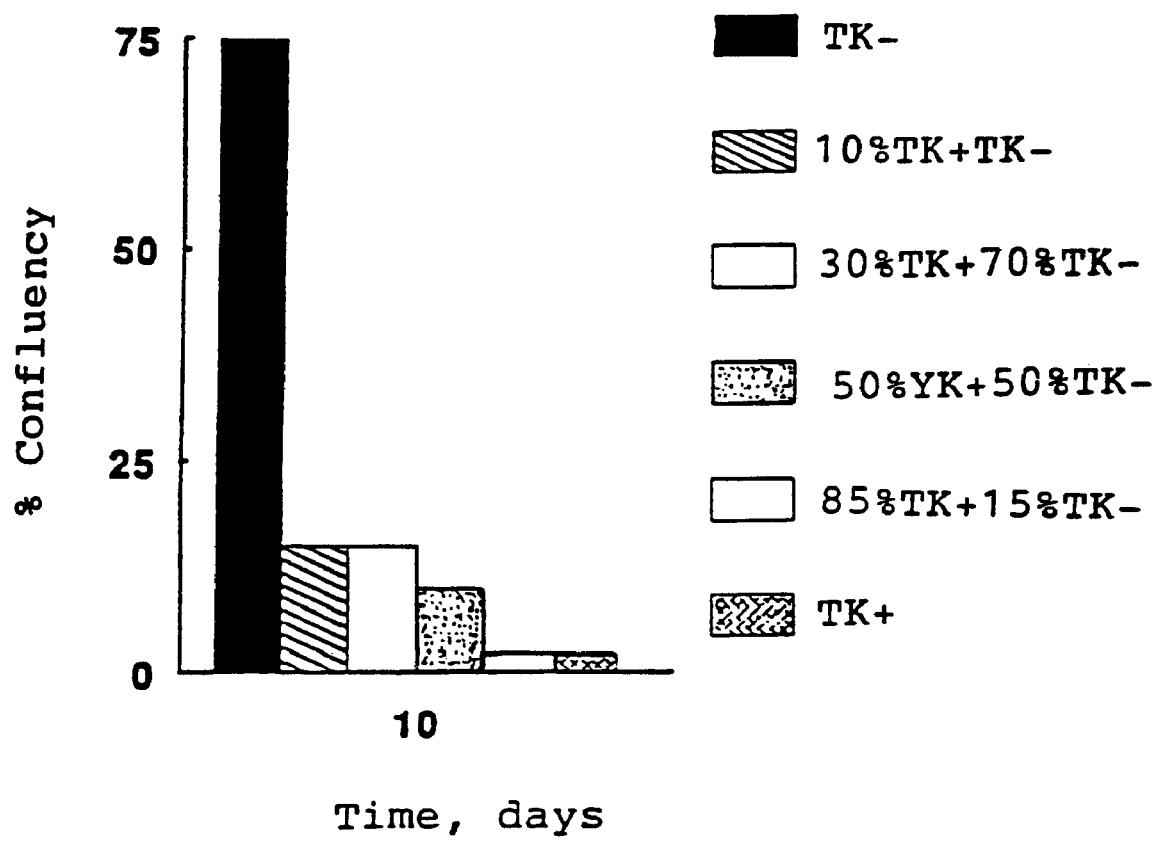

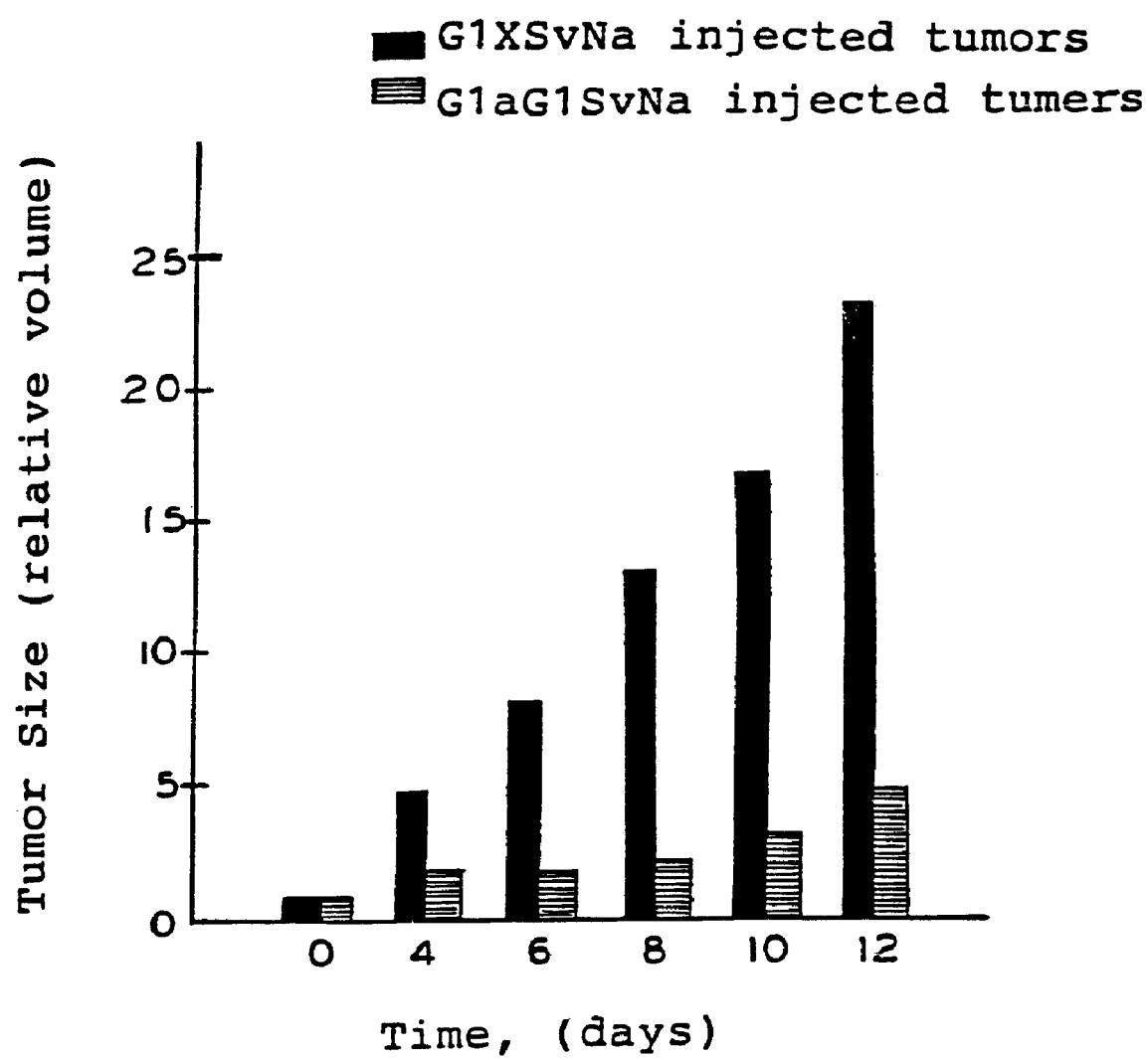

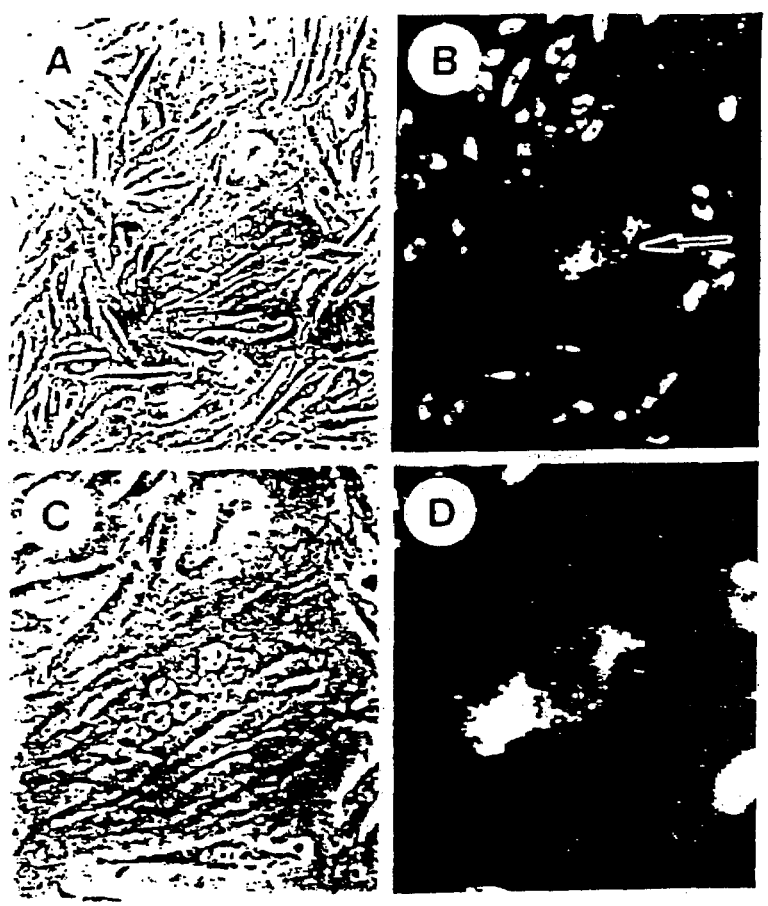
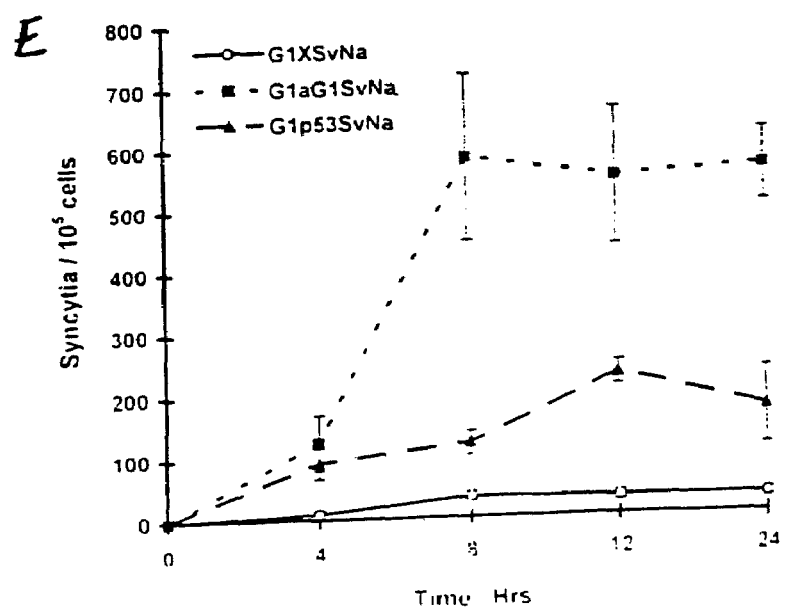
Fig. 17

SEQUENCE LISTING

<160> NUMBER OF SEQ ID NOS: 2

<210> SEQ ID NO 1
<211> LENGTH: 2219
<212> TYPE: DNA
<213> ORGANISM: Homo sapiens

<400> SEQUENCE: 1

```
acaactgact ctcagaaact gctacaccag ctgaatgccc tgttggaaca ggagtctaga      60
tgtcagccaa aggtctgtgg tttgagacta attgagtctg cacacgataa tggcctcaga     120
atgactgcaa gactaaggga ctttgaagta aaagatcttc ttagtctaac tcagttcttt     180
ggctttgaca cagagacatt ttctctagct gtgaatttac tggacagatt cctgtctaaa     240
atgaaggtac agcccaagca ccttgggtgt gttggactga gctgctttta tttggctgta     300
aaatcaatag aagaggaaag gaatgtccca ttggcaactg acttgatccg aataagtcaa     360
tataggttta cggtttcaga cttgatgaga atggaaaaga ttgtattgga gaaggtgtgt     420
tggaaagtca aagctactac tgcctttcaa tttctgcaac tgtattattc actccttcaa     480
gagaacttgc cacttgaaag gagaaatagc attaattttg aaagactaga agctcaactg     540
aaggcatgtc attgcaggat catattttct aaagcaaagc cttctgtgtt ggcattgtct     600
atcattgcat tagagatcca agcacagaag tgtgtagagt taacagaagg aatagaatgt     660
```

-continued

```
cttcagaaac attccaagat aaatggcaga gatctgacct tctggcaaga gcttgtatcc    720
aaatgtttaa ctgaatattc atcaaataag tgttccaaac caaatgttca gaagttgaaa    780
tggattgttt ctgggcgtac tgcacggcaa ttgaagcata gctactacag ataactcac     840
cttccaacaa ttcctgaaat ggtcccttaa ctggattatt acagcaccaa aaacttctc     900
tgaagccttt ctccacaacc ttgttctatg gattccataa tgttacaatg gatttaagct    960
atgaagcctc aaaacatcac gagataagca tgatggtctc agacttggga aaactgccta   1020
atattatgct gtagtggaat tatgtttaga tttgaattca tctgtgaagc attcaaagca   1080
aagctaaaag cctaaatgtg aaatgctaat gacaagcctg agaaggtaaa ctgtgaatct   1140
tcatttctat cattgatcta actttagata ttggatcaat atatttaggt ggtattgaaa   1200
atgctattgg aggagtcaca ctaatactat caactatcag tcttcccaca gcttcaatca   1260
ctgtcattat tctaatccta ctcctactta aattttaagt tatgaggttt atgtcaaaag   1320
caacatttca caaatgtact tttaaggcat aataagggtt aacattctag gcagtataaa   1380
cacacccat aatgcaagta ataggtaatc tagagatgtg gactttattg ctatatggga    1440
attacattta aatttgaggg catttatata agaaatacag acctataagt tggcatattc   1500
attaagttat ctttaatatt tttctagaaa caggtgacat ttgatctatc gataaaattt   1560
tatacagaac ctactgcctc aaactgaatc ccatcaagaa aactagtttc tattgtatta   1620
gtaactcaaa ataaattatc acttcgaaaa cttgctttcc cacactaagg taagttcaga   1680
ctagattgaa cactccagaa ttttttacta cagactgttt ttaagttaga agtgatggca   1740
attttataaa tagagaatat acttccactg atgcccttac tgtgccaaaa caaaaatctt   1800
aagaaaagca agtagacacc ttcataacta tgaatgaagc tgctgaagta gtgtttagga   1860
tcctccatgg cagttagtga atgtaagaag tacagtgtta aagtgttgta aacagttact   1920
cagtgcaatg tatagcctga gtctatccat gatggctata tccaatttga catcacgtta   1980
tggatcagta cacaatgaaa aaccaaagaa ccacgtatat cttattctta acttttgtaa   2040
accatgtttt atgggtaact ttttagtttt cccaaaaggc tgataaattt caatattttg   2100
aatacatcat tgttaatttt gagttggcag aggtaaacta accaactacc attatgtttt   2160
agtactaagg gatataacctt tcaataaagt taatgaaatt caaaaaaaaa aaaaaaaa    2219
```

<210> SEQ ID NO 2
<211> LENGTH: 249
<212> TYPE: PRT
<213> ORGANISM: Homo sapiens

<400> SEQUENCE: 2

```
Met Thr Ala Arg Leu Arg Asp Phe Glu Val Lys Asp Leu Leu Ser Leu
 1               5                  10                  15

Thr Gln Phe Phe Gly Phe Asp Thr Glu Thr Phe Ser Leu Ala Val Asn
                20                  25                  30

Leu Leu Asp Arg Phe Leu Ser Lys Met Lys Val Gln Pro Lys His Leu
            35                  40                  45

Gly Cys Val Gly Leu Ser Cys Phe Tyr Leu Ala Val Lys Ser Ile Glu
        50                  55                  60

Glu Glu Arg Asn Val Pro Leu Ala Thr Asp Leu Ile Arg Ile Ser Gln
65                  70                  75                  80

Tyr Arg Phe Thr Val Ser Asp Leu Met Arg Met Glu Lys Ile Val Leu
                85                  90                  95
```

-continued

```
Glu Lys Val Cys Trp Lys Val Lys Ala Thr Thr Ala Phe Gln Phe Leu
            100             105             110

Gln Leu Tyr Tyr Ser Leu Leu Gln Glu Asn Leu Pro Leu Glu Arg Arg
        115             120             125

Asn Ser Ile Asn Phe Glu Arg Leu Glu Ala Gln Leu Lys Ala Cys His
        130             135             140

Cys Arg Ile Ile Phe Ser Lys Ala Lys Pro Ser Val Leu Ala Leu Ser
145             150             155             160

Ile Ile Ala Leu Glu Ile Gln Ala Gln Lys Cys Val Glu Leu Thr Glu
            165             170             175

Gly Ile Glu Cys Leu Gln Lys His Ser Lys Ile Asn Gly Arg Asp Leu
            180             185             190

Thr Phe Trp Gln Glu Leu Val Ser Lys Cys Leu Thr Glu Tyr Ser Ser
        195             200             205

Asn Lys Cys Ser Lys Pro Asn Val Gln Lys Leu Lys Trp Ile Val Ser
        210             215             220

Gly Arg Thr Ala Arg Gln Leu Lys His Ser Tyr Tyr Arg Ile Thr His
225             230             235             240

Leu Pro Thr Ile Pro Glu Met Val Pro
                245
```

EXPRESSION OF CYCLIN G1 IN TUMORS

CROSS-REFERENCE

This application is a continuation of application Ser. No. 10/218,542, filed Aug. 14, 2002 now abandoned, which is a continuation of Ser. No. 09/066,294, filed Oct. 26, 1998 now abandoned, which is a 371 National Phase of PCT/US96/17442, filed on Oct. 31, 1996, which is a continuation-in-part of application Ser. No. 08/551,486, filed Nov. 1, 1995 now abandoned, the contents of which are hereby incorporated by reference.

This invention relates to the expression of cyclin G1 in tumors. More particularly, this invention relates to: (i) the treatment of tumors such as osteogenic sarcoma or Ewing's sarcoma, by inhibiting cyclin G1 protein in the tumor cells; (ii) the prevention of restenosis by inhibiting cyclin G1 protein in cells at the site of an invasive vascular procedure or vascular lesion; (iii) the immortalization of cells by transducing such cells with a polynucleotide encoding cyclin G1 protein; (iv) making cells more receptive to infection or transduction by a retroviral vector by transfecting the cells with a polynucleotide encoding cyclin G1 protein, prior to or concurrently with said retroviral transduction or infection; and (v) a method of detecting cancer by determining the level of expression of cyclin G1 protein in cells. This invention also relates to expression vehicles, preferably retroviral vectors and adenoviral vectors, which include polynucleotides encoding agents which inhibit cyclin G1 protein, such as antisense polynucleotides, and antibodies or fragments or derivatives thereof which recognize cyclin G1 protein, and to expression vehicles which include a polynucleotide encoding cyclin G1 protein.

BACKGROUND OF THE INVENTION

Genes encoding a new class of proteins known as cyclins have been identified as a new class of protooncogenes, and cyclin-dependent kinase (or Cdk) inhibitors have been identified as tumor suppressors, thereby uniting the molecular mechanisms of cellular transformation and tumorigenesis with the enzymology governing cell cycle control. (Hall, et al., *Curr. Opin. Cell Biol.*, Vol. 3, pgs. 176-184 (1991); Hunter, et al., *Cell*, Vol. 55, pgs. 1071-1074 (1991); Hunter, et al., *Cell*, Vol. 79; pgs. 573-582 (1994); Elledge, et al., *Curr. Opin. Cell Biol.*, Vol 6, pgs. 874-878 (1994); Peter, et al., *Cell*, Vol. 79, pgs. 181-184 (1994)). The sequential expression of specific cyclins and the essential functions of specific Cdk complexes have been defined (Wu, et al., *Int. J. Oncol.*, Vol. 3, pgs. 859-867 (1993); Pines, et al., *New Biologist*, Vol. 2, pgs 389-401 (1990); Pines, *Cell Growth and Differentiation*, Vol. 2, pgs. 305-310 (1991); Reed, *Ann. Rev. Cell Biol.*, Vol. 8, pgs. 529-561 (1992); Sherr, *Cell*, Vol. 79, pgs. 551-555 (1994)), thereby providing direct links to the fundamental mechanisms of DNA replication, transcription, repair, genetic instability, and apoptosis. (D'Urso, et al., *Science*, Vol. 250, pgs. 786-791 (1990); Wu, et al., *Oncogene*, Vol. 9, pgs 2089-2096 (1994); Roy, *Cell*, Vol. 79, pgs. 1093-1101 (1994); Meikrantz, et al., *Proc. Nat. Acad. Sci.*, Vol. 91, pgs. 3754-3758 (1994)). Both the universal Cdk inhibitor p21/WAF1/CIP1 (Xiong, et al., *Nature*, Vol. 366, pgs. 701-704 (1993); Harper, et al., *Mol. Biol. Cell*, Vol. 6, pgs. 387-400 (1995)), and cyclin G1 (Wu, et al., *Oncol. Reports*, Vol. 1, pgs, 705-711 (1994)) are induced by the wild-type p53 tumor suppressor protein in the initiation of DNA repair and/or apoptosis. (E1-Deiry, et al., *Cell*, Vol. 75, pgs 817-825 (1993); E1-Deiry, et al., *Cancer Res.*, Vol. 54, pgs. 1169-1174 (1994)). Thus, the molecular components regulating critical cell cycle checkpoints represent strategic targets for potential therapeutic intervention in the treatment of cell proliferation disorders, including pediatric bone cancers, in which the Rb and the p53 tumor suppressor genes often are inactivated. (Hansen, et al., *Proc. Nat. Acad. Sci.*, Vol. 82, pgs. 6216-6220 (1985); Toguchida, et al., *Nature*, Vol. 338, pgs. 156-158 (1989); Toguchida, et al., *Cancer Res.*, Vol. 48, pgs. 3939-3943 (1988); Diller, et al., *Mol. Cell. Biol.*, Vol. 10, pgs. 5772-5781 (1990)). Previous studies have characterized the progressive profile of cyclin expression and Cdk activation (Wu, 1993; Carbonaro-Hall, et al., *Oncogene*, Vol. 8, pgs 1649-1659 (1993); Hall, et al., Oncogene, Vol. 8, pgs. 1377-1384 (1993); Williams, et al., *J. Biol. Chem.*, Vol. 268, pgs. 8871-8880 (1993); Albers, et al., *J. Biol. Chem.*, Vol. 268, pgs. 22825-22829 (1993)), as well as the p53-independent induction of p21/WAF1/CIP1 (Wu, et al., *Oncol. Reports*, Vol. 2, pgs 227-231 (1995)), in MG-63 osteosarcoma cells. Also, antisense oligonucleotide strategies directed against cyclin D1 effectively inhibit cell cycle progression in these osteosarcoma cells. (Wu, 1993).

Metastatic carcinoma is an important target for gene therapy as it is associated with poor outcome. Colorectal cancer, for example, is the second leading cause of cancer death in the United States after lung cancer, followed by breast and pancreatic cancer (Silberberg et al., *Cancer Clin.*, Vol. 40, pgs. 9-26 (1990)). Of these carcinomas, pancreatic cancer has the worst prognosis. The median survival of patients with metastatic pancreatic cancer is three to six months and virtually all the patients are dead within a year (Merrick et al., *Gastroenterol. Clin. N. Amer.*, Vol. 19, pgs. 935-962 (1990)). Approximately 40% of patients will have metastatic disease either to the liver or the peritoneal cavity or both at the time of diagnosis. Chemotherapy for metastatic disease is ineffective despite multimodal therapy. Hence, alternative approaches to metastatic carcinoma would be desirable.

Wu, et al. (*Oncol. Reports*, Vol. 1, pgs. 705-711 (1994)), hereinabove mentioned, discloses the deduced amino acid sequence and cDNA sequence for human cyclin G1 protein. Wu, et al., also disclose that higher levels of cyclin G1 expression were found in osteosarcoma cells and in Ewing's sarcoma cells than in normal diploid human fibroblasts. Although Wu, et al., state that the overexpression of cyclin G1 protein in human osteosarcoma cells provides a potential link to cancer, Wu, et al., do not disclose the treatment of cancer by interfering with or inhibiting the function of cyclin G1 protein in cancer cells.

SUMMARY OF THE INVENTION

Applicants have discovered that by interfering with and/or inhibiting the function or expression of cyclin G1 protein in cancer cells, one may inhibit, prevent, or destroy the growth and/or survival of such cancer cells. Thus, the present invention is directed to the treatment of a tumor (preferably a cancerous tumor) by inhibiting cyclin G1 protein, preferably through the administration of antisense oligonucleotides to a polynucleotide encoding cyclin G1 protein, or antibodies to cyclin G1 protein.

In addition, the present invention is directed to (i) the prevention of restenosis by inhibiting cyclin G1 protein in cells at the site of an invasive vascular procedure or vascular lesion; (ii) the immortalization of cells by transducing cells with a polynucleotide encoding cyclin G1 protein; (iii) the transducing of cells with a polynucleotide encoding cyclin G1 protein in order to make cells more receptive to transduction or infection with a retroviral vector; and (iv) a cancer assay which involves detection of cyclin G1 protein and/or a polynucleotide encoding such protein.

The present invention also is directed to expression vehicles which include polynucleotides encoding agents which inhibit cyclin G1 protein, and to expression vehicles which include a polynucleotide encoding cyclin G1 protein. Such expression vehicles include, but are not limited to, viral vectors such as retroviral vectors and adenoviral vectors.

BRIEF DESCRIPTION OF THE DRAWINGS

The invention now will be described with respect to the drawings, wherein:

FIG. 1. is a nucleotide sequence of human cyclin G1 cDNA (SEQ ID NO:1) which encodes human cyclin G1 protein with amino acid sequence ID NO:2;

FIG. 2 depicts the staining of MG-63 osteogenic sarcoma cells following transduction of such cells with a retroviral vector including a B-galactosidase, or lacZ gene;

FIG. 3 is a graph of the degrees of confluency (%) in mixtures of MG-63 cells which were transduced with a retroviral vector including a Herpes Simplex Virus thymidine kinase (TK) gene, and cells which were not transduced with such vector;

FIG. 6 is a Western Blot of expression of p29 cyclin G1 protein in MG-63 cells transduced with G1XSvNa, G1aG1SvNa, or G1aD1SvNa;

FIG. 14 is a graph of tumor sizes in mice injected with MNNG/HOS cells, followed by injection of the retroviral vectors G1XSvNa or G1aG1SvNa. Tumor volumes are measured at 0, 4, 6, 8, 10, and 12 days after injection of the retroviral vectors.

DETAILED DESCRIPTION OF THE INVENTION

Figure 4:
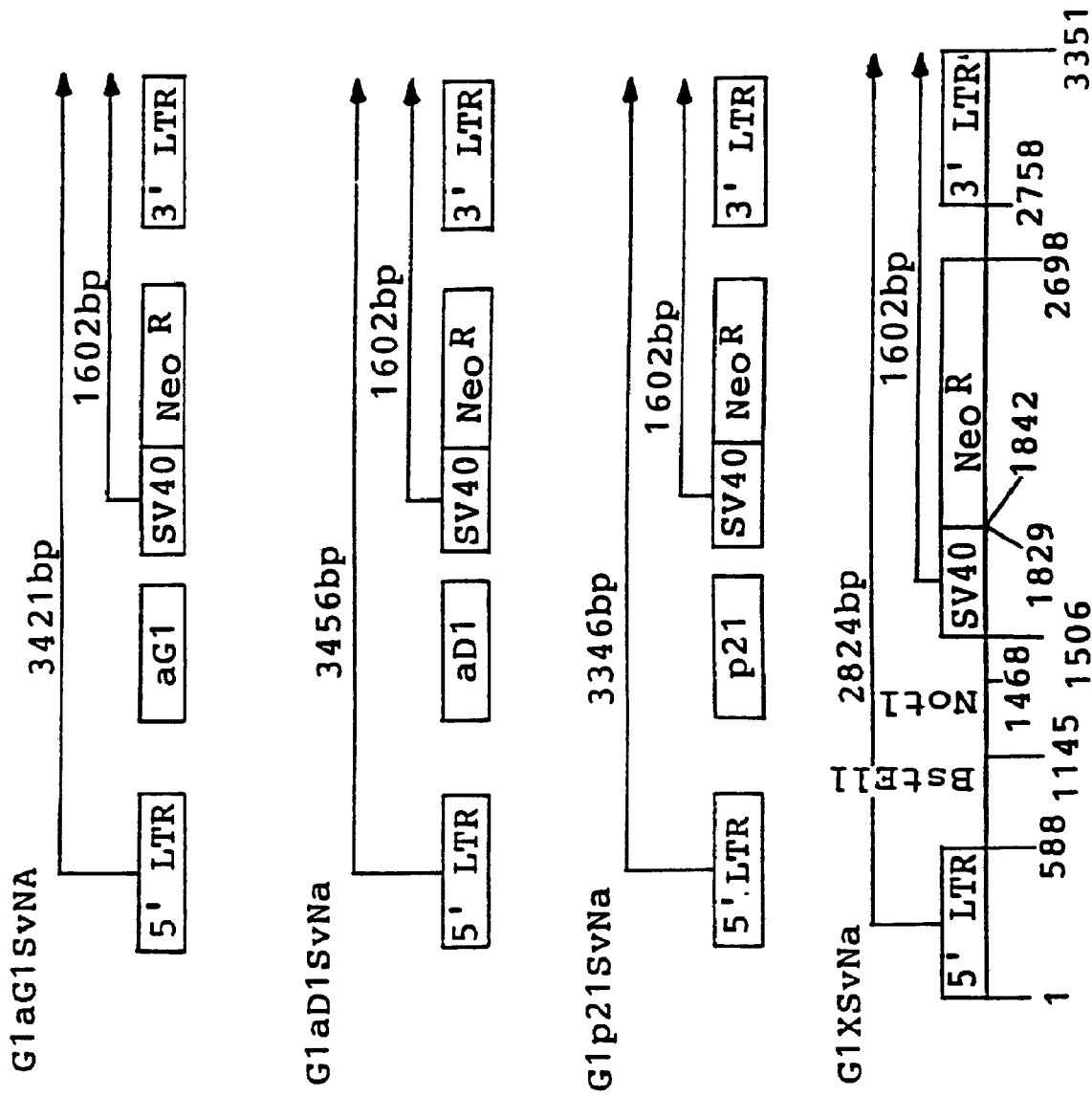
FIG. 4 is a schematic of the retroviral vectors G1aD1SvNa, G1aG1SvNa, G1p21SvNa, and G1XSvNa.

In accordance with an aspect of the present invention, there is provided a method of treating a tumor in a host. The method comprises administering to a host or to the tumor an agent which inhibits cyclin G1 protein. The agent is administered in an amount effective to inhibit cyclin G1 protein in the tumor cells.

The term "treating a tumor" as used herein means that one provides for the inhibition, prevention, or destruction of the growth of the tumor cells.

The term "inhibit cyclin G1 protein" as used herein, means that the agent inhibits or prevents the expression of a polynucleotide encoding cyclin G1 protein, or inhibits or prevents the function of cyclin G1 protein.

Agents which inhibit cyclin G1 protein which may be employed include, but are not limited to, polynucleotides (including antisense oligonucleotides or polynucleotide fragments or sequences which are complementary to at least a portion of a polynucleotide encoding cyclin G1 protein) which bind to a polynucleotide encoding cyclin G1 protein to prevent expression of a polynucleotide encoding cyclin G1 protein, and antagonists to cyclin G1 protein, such as, for example, antibodies or fragments or derivatives thereof which recognize cyclin G1 protein, and cyclin-dependent kinase inhibitors.

In one embodiment, the agent which inhibits cyclin G1 protein is a polynucleotide which binds to a polynucleotide encoding cyclin G1 protein, and in particular is an antisense polynucleotide which is complementary to at least a portion of a polynucleotide encoding cyclin G1 protein. A nucleotide cDNA (FIG. 1) and deduced amino acid sequence of human cyclin G1 protein is described in Wu, et al., *Oncology Reports*, Vol. 1, pgs. 705-711 (1994), which is incorporated herein by reference.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

In general, the antisense polynucleotide which is complementary to at least a portion of a polynucleotide encoding cyclin G1 protein includes at least 15 nucleotides, preferably at least 18 nucleotides, and more preferably from 18 to 20 nucleotides. In one embodiment, the antisense polynucleotide is complementary to the entire length of the polynucleotide encoding cyclin G1 protein.

In one embodiment, the antisense polynucleotide is complementary to, and thus capable of binding or hybridizing to, at least a portion of mRNA encoding cyclin G1 protein, thereby inhibiting translation of such mRNA. In another embodiment, the antisense polynucleotide is complementary to, and thus capable of binding or hybridizing to, single-stranded or double-stranded DNA encoding cyclin G1 protein, thereby preventing the transcription of such DNA to mRNA, or inhibiting the replication of such DNA. The antisense polynucleotide may bind to any portion of the DNA or mRNA encoding cyclin G1 protein, but preferably such antisense polynucleotide binds at the 5' end of the DNA or mRNA.

In another embodiment, the antisense polynucleotide may be a ribozyme that promotes the cleavage of mRNA encoding cyclin G1. As used herein, the term "ribozyme" means any single strand of polynucleotide that forms a secondary structure which promotes the catalytic cleavage of a target mRNA molecule once specific sequence-based recognition of the target mRNA is achieved.

The antisense oligonucleotide may be synthesized according to techniques known to those skilled in the art, such as, for example, by an automatic oligonucleotide synthesizer. The antisense oligonucleotide then is administered to a host in an amount effective to inhibit the expression of a polynucleotide encoding cyclin G1 protein in tumor cells of a host. The antisense oligonucleotide may be administered in an amount of from about 0.1 µM to about 10 µM, preferably from about 1 µM to about 5 µM. The host may be an animal host, and in particular a mammalian host, including human and non-human primate hosts. The antisense oligonucleotide in general is administered to the host systemically in conjunction with an acceptable pharmaceutical carrier, such as physiological saline. Alternatively, the antisense oligonucleotides may be contained within liposomes, which are administered to the host systemically in conjunction with an acceptable pharmaceutical carrier. Such systemic administration may be, for example, by intravenous, intraarterial, or intraperitoneal administration. Alternatively, the antisense oligonucleotide may be administered directly to the tumor.

The antisense oligonucleotides may be modified in order to stabilize the oligonucleotide against degradation by nucleases and/or to enhance the ability of the antisense oligonucleotide to penetrate the tumor cells. Such modification may be accomplished by substituting at least one of the phosphodiester bonds of the antisense oligonucleotide with a structure which provides for increased stabilization of the antisense oligonucleotide against degradation by nucleases and/or enhances the ability of the antisense oligonucleotide to penetrate the tumor cells. Such substitutions may include phosphorothioate and phosphorodithioate bonds, phosphotriesters, alkyl or aryl phosphonate bonds, such as methylphosphonate bonds, short chain alkyl or cycloalkyl structures or short chain heteroatomic or heterocyclic structures, such as, for example, $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$, and O—N($CH_3$)—$CH_2$—$CH_2$, as well as morpholino structures. Examples of such modifications are described in PCT Application No. WO93/05182, published Mar. 18, 1993, and in U.S. Pat. No. 5,034,506, issued Jul. 23, 1991. Examples of alkyl or aryl phosphonate bonds also are described in U.S. Pat. Nos. 4,469,863 and 4,511,713. Alternatively, at least one nucleotide of the antisense oligonucleotide may be conjugated to a moiety which may be an amino acid; a dipeptide mimic, a sugar; a sugar phosphate; a neurotransmitter; a hydrophilic polymer such as polyhydroxypropylmethacrylamide, dextrans, polymaleic anhydride, a cyclodextrin, a starch, or polyethyleneimine. Examples of such moieties are described in PCT Application No. WO94/01448, published Jan. 20, 1994. Further examples of moieties which may be employed in modifying the antisense oligonucleotide include, but are not limited to, alkyl- or arylphosphorates, carbamates, sulfamates, and (thio)formacetal.

The above modifications may be made to the antisense oligonucleotide during synthesis of the antisense oligonucleotide by means known to those skilled in the art. In a preferred embodiment, when the antisense oligonucleotide is administered directly or in a liposome, the antisense oligonucleotide includes at least one phosphorothioate or phosphorodithioate linker moiety, which may be attached to the backbone of the antisense oligonucleotide during synthesis by techniques known to those skilled in the art.

In another embodiment, the antisense oligonucleotide is administered to the host by transducing tumor cells of the host with a polynucleotide encoding an antisense polynucleotide which is complementary to at least a portion of a polynucleotide encoding cyclin G1 protein. The polynucleotide encoding an antisense polynucleotide which is complementary to at least a portion of a polynucleotide encoding cyclin G1 protein may be contained within an appropriate expression vehicle which is transduced into the tumor cell. Such expression vehicles include, but are not limited to, plasmids, eukaryotic vectors, prokaryotic vectors (such as, for example, bacterial vectors), and viral vectors.

In one embodiment, the vector is a viral vector. Viral vectors which may be employed include RNA virus vectors (such as retroviral vectors), and DNA virus vectors (such as adenoviral vectors, adeno-associated virus vectors, Herpes Virus vectors, and vaccinia virus vectors). When an RNA virus vector is employed, in constructing the vector, the polynucleotide encoding the antisense polynucleotide is in the form of RNA. When a DNA virus vector is employed, in constructing the vector, the polynucleotide encoding the antisense polynucleotide is in the form of DNA.

In one embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. The vector is generally a replication incompetent retrovirus particle.

Retroviral vectors are useful as agents to mediate retroviral-mediated gene transfer into eukaryotic cells. Retroviral vectors are generally constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. Alternatively, two genes may be expressed from a single promoter by the use of an Internal Ribosome Entry Site.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

Examples of retroviral vectors which may be employed include retroviral vectors generated from retroviral plasmid vectors derived from retroviruses including, but not limited to, Moloney Murine Leukemia Virus vectors such as those described in Miller, et al., *Biotechniques*, Vol. 7, pgs. 980-990 (1989), and in Miller, et al., *Human Gene Therapy*, Vol. 1, pgs. 5-14 (1990).

In a preferred embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. patent application Ser. No. 08/340,805, filed Nov. 17, 1994, and in PCT Application No. WO91/10728, published Jul. 25, 1991, and incorporated herein by reference in their entireties.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having Ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The retroviral plasmid vector then is employed to transduce a packaging cell line to form a producer cell line. Examples of packaging cells which may be transfected include, but are not limited to, the PE501, PA317, ψ-2, ψ-AM, PA12, T19-14X, VT-19-17-H2, ψ CRE, ψ CRIP, GP+E-86, GP+envAm12, and DAN cell lines, as described in Miller, *Human Gene Therapy*, Vol. 1, pgs. 5-14 (1990). The retroviral plasmid vector containing the polynucleotide encoding the antisense polynucleotide, which is complementary to at least a portion of a polynucleotide encoding cyclin G1 protein, transduces the packaging cells through any means known in the art. Such means include, but are not limited to, electroporation, the use of liposomes, and $CaPO_4$ precipitation.

The packaging cells thus become producer cells which generate retroviral vectors which include a polynucleotide encoding an antisense polynucleotide which is complementary to at least a portion of a polynucleotide encoding cyclin G1 protein. Such retroviral vectors then are transduced into the tumor cells, whereby the transduced tumor cells will produce the antisense polynucleotide, which is complementary to at least a portion of the polynucleotide encoding cyclin G1 protein.

The retroviral vectors are administered to a host in an amount which is effective to inhibit, prevent, or destroy the growth of the tumor cells through inhibition of the expression of the polynucleotide encoding cyclin G1 protein in the tumor cells. Such administration may be by systemic administration as hereinabove described, or by direct injection of the retroviral vectors in the tumor. In general, the retroviral vectors are administered in an amount of at least $1\times10^5$ cfu/ml, and in general, such an amount does not exceed $1\times10^9$ cfu/ml. Preferably, the retroviral vectors are administered in an amount of from about $1\times10^6$ cfu/ml to about $1\times10^8$ cfu/ml. The exact dosage to be administered is dependent upon a variety of factors including the age, weight, and sex of the patient, and the size and severity of the tumor being treated.

The retroviral vectors also may be administered in conjunction with an acceptable pharmaceutical carrier, such as, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.). The selection of a suitable pharmaceutical carrier is deemed to be apparent to those skilled in the art from the teachings contained herein.

In another alternative, retroviral producer cells, such as those derived from the packaging cell lines hereinabove described, which include a polynucleotide encoding an antisense polynucleotide, which is complementary to at least a portion of a polynucleotide encoding cyclin G1 protein, may be administered to a host. Such producer cells may, in one embodiment, be administered systemically (e.g., intravenously or intraarterially) at a point in close proximity to the tumor, or the producer cells may be administered directly to the tumor. The producer cell line then produces retroviral vectors including a polynucleotide encoding an antisense polynucleotide which is complementary to a polynucleotide encoding cyclin G1 protein, in vivo, whereby such retroviral vectors then transduce the tumor cells.

In another embodiment, the agent which inhibits cyclin G1 protein is an antagonist to cyclin G1 protein which binds to and inhibits cyclin G1 protein. Examples of antagonists to cyclin G1 protein include, but are not limited to, antibodies or fragments or derivatives thereof which recognize cyclin G1 protein, and small molecules, such as, for example, cyclin-dependent kinase inhibitors which bind to and inhibit the function of cyclin G1 protein.

In one embodiment the antagonist is an antibody or fragment or derivative thereof which recognizes cyclin G1 protein. The term "fragment or derivative thereof," means an antibody having deletions and/or substitutions of amino acid residues with respect to the unmodified antibody, yet such fragment or derivative recognizes cyclin G1 protein. Such antibody may be a monoclonal or polyclonal antibody. In one embodiment, the antibody is a single chain antibody.

Preferably, the antibody is administered to the host such that the antibody or fragment or derivative thereof enters the tumor cells. In a preferred embodiment, the antibody or fragment or derivative thereof which recognizes cyclin G1 protein is administered to the host by transducing tumor cells of the host with a polynucleotide encoding the antibody or fragment or derivative thereof which recognizes cyclin G1 protein. The polynucleotide may be contained in an appropriate expression vehicle such as those hereinabove described. In one embodiment, the polynucleotide is contained in a retroviral vector, which may be a retroviral vector as hereinabove described.

The vector, which includes the polynucleotide encoding an antibody or fragment or derivative thereof which recognizes cyclin G1 protein is administered to the host in an amount effective to inhibit the function of the cyclin G1 protein in the tumor cells in the host. When a retroviral vector is employed, such retroviral vector is administered in an amount of from about $1\times10^6$ cfu/ml to about $1\times10^8$ cfu/ml. Such vector may be administered systemically (such as, for example, by intravenous, intraarterial, or intraperitoneal administration) or, alternatively, the vector may be administered directly to the tumor. The vectors then transduce the tumor cells, whereby the antibody or fragment or derivative thereof which recognizes cyclin G1 protein is expressed in the tumor cells. Such antibody or fragment or derivative thereof will bind to the cyclin G1 protein in the tumor cells, thereby inhibiting the function of the cyclin G1 protein in the tumor cells.

Tumors which may be treated in accordance with the present invention, through the inhibition of cyclin G1 protein, include non-malignant, as well as malignant, or cancerous tumors. Cancerous tumors which may be treated include, but are not limited to, osteogenic sarcoma and Ewing's sarcoma and other neoplastic disorders in which cyclin G1 is expressed, such as, glioblastoma, neuroblastoma, breast cancer, prostate cancer, leukemias, lymphomas (including Hodgkin's and non-Hodgkin's lymphoma), fibrosarcoma, rhabdomyosarcoma, colon cancer, pancreatic cancer, liver cancers such as hepatocellular carcinoma, and adenocarcinomas.

The above treatments, in which cyclin G1 is inhibited, also may be employed in combination with other treatments of tumors, such as, for example, (i) radiation; (ii) chemotherapy; or (iii) the transduction of the tumor cells with a polynucleotide encoding a negative selective marker, such as, for example, a viral thymidine kinase gene, followed by the administration of an interaction agent, such as, for example, ganciclovir, which kills the cells transduced with the polynucleotide encoding the negative selective marker.

In one embodiment, an agent which inhibits cyclin G1 protein is administered to a host in accordance with one of the methods hereinabove described. The growth of any tumor cells which contain the agent will be inhibited, prevented or destroyed. In addition, the tumor cells are transduced with a polynucleotide encoding a negative selective marker or "suicide" gene. The polynucleotide encoding the negative selective marker may be contained in an expression vehicle such as those hereinabove described. Once the tumor cells are transduced with the polynucleotide encoding the negative selective marker, an interaction agent is administered to the host, whereby the interaction agent interacts with the negative selective marker in order to prevent, inhibit, or destroy the growth of the tumor cells.

Negative selective markers which may be employed include, but are not limited to, thymidine kinase, such as Herpes Simplex Virus thymidine kinase, cytomegalovirus thymidine kinase, and varicella-zoster virus thymidine kinase; and cytosine deaminase.

In one embodiment, the negative selective marker is a viral thymidine kinase selected from the group consisting of Herpes Simplex Virus thymidine kinase, cytomegalovirus thymidine kinase, and varicella-zoster virus thymidine kinase. When such viral thymidine kinases are employed, the interaction or chemotherapeutic agent preferably is a nucleoside analogue, for example, one selected from the group consisting of ganciclovir, acyclovir, and 1-2-deoxy-2-fluoro-β-D-arabinofuranosil-5-iodouracil (FIAU). Such interaction agents are utilized efficiently by the viral thymidine kinases as substrates, and such interaction agents thus are incorporated lethally into the DNA of the tumor cells expressing the viral thymidine kinases, thereby resulting in the death of the tumor cells.

In another embodiment, the negative selective marker is cytosine deaminase. When cytosine deaminase is the negative selective marker, a preferred interaction agent is 5-fluorocytosine. Cytosine deaminase converts 5-fluorocytosine to 5-fluorouracil, which is highly cytotoxic. Thus, the tumor cells which express the cytosine deaminase gene convert the 5-fluorocytosine to 5-fluorouracil and are killed.

The interaction agent is administered in an amount effective to inhibit, prevent, or destroy the growth of the transduced tumor cells. For example, the interaction agent may be administered in an amount from 5 mg to 10 mg/kg of body weight, depending on overall toxicity to a patient. The interaction agent preferably is administered systemically, such as, for example, by intravenous administration, by parenteral administration, by intraperitoneal administration, or by intramuscular administration.

When an expression vehicle, such as those hereinabove described, including a negative selective marker is administered to tumor cells, a "bystander effect" may result, i.e., tumor cells which were not originally transduced with the nucleic acid sequence encoding the negative selective marker may be killed upon administration of the interaction agent. Although Applicants do not intend to be limited to any theoretical reasoning, the transformed tumor cells may be producing a diffusible form of the negative selective marker that either acts extracellularly upon the interaction agent, or is taken up by adjacent, non-transformed tumor cells, which then become susceptible to the action of the interaction agent. It also is possible that one or both of the negative selective marker and the interaction agent are communicated between tumor cells.

Agents which inhibit cyclin G1 protein also may prevent vascular restenosis after invasive vascular procedures such as angioplasty, vascular grafts, such as arterial grafts, or coronary bypass surgery. Thus, in accordance with another aspect of the present invention, there is provided a method of preventing restenosis which comprises administering to a host, or to the site of an invasive vascular procedure or vascular lesion, an agent which inhibits cyclin G1 protein. The agent is administered in an amount effective to prevent restenosis in a host. The agent may be administered during or after the invasive vascular procedure. The term "invasive vascular procedure" as used herein means any procedure which involves repair, removal, replacement and/or redirection (e.g., bypass or shunt) of a portion of the vascular system including but not limited to arteries and veins. Such procedures include, but not limited to, angioplasty, vascular grafts such as arterial grafts, removals of blood clots, removals of portions of arteries or veins, and coronary bypass surgery.

Agents which inhibit cyclin G1 protein which may be employed include, but are not limited to, those hereinabove described. Preferably, the agent which inhibits cyclin G1 protein is an antisense polynucleotide which is complementary to, and thus is capable of binding or hybridizing to, at least a portion of a polynucleotide encoding cyclin G1 protein as hereinabove described. Such antisense oligonucleotide may have a length as hereinabove described and be administered in an amount effective to prevent restenosis. Such amount may be as hereinabove described. The antisense oligonucleotide may be administered intravascularly and may be administered directly to the site of the invasive vascular procedure or the vascular lesion.

In a preferred embodiment, the antisense oligonucleotide is administered to the host by transducing vascular cells at the site of an invasive vascular procedure or a vascular lesion with a polynucleotide encoding an antisense polynucleotide which is complementary to at least a portion of a polynucleotide encoding cyclin G1 protein. Such polynucleotide encoding the antisense polynucleotide may be contained in an appropriate expression vehicle as hereinabove described, which is transduced into the cells of the site of an invasive vascular procedure or vascular lesion. In one embodiment, the expression vehicle is a viral vector such as those hereinabove described. In one embodiment, the viral vector is a retroviral vector, which may be as hereinabove described.

When a retroviral vector is employed, such retroviral vector is administered in an amount hereinabove described, and is administered intravascularly. In one embodiment, the retroviral vector is administered to the site of the invasive vascular procedure or vascular lesion. The vectors transduce the vascular cells at the site of the invasive vascular procedure or vascular lesion, whereby the antisense oligonucleotide is produced in such cells, thereby inhibiting the expression of a polynucleotide encoding cyclin G1 in such cells and thus preventing restenosis by preventing the proliferation of such cells.

In another embodiment, the agent which inhibits cyclin G1 protein is an antagonist to cyclin G1 protein which binds to and inhibits cyclin G1 protein as hereinabove described, and in one embodiment may be an antibody or fragment or derivative thereof which recognizes cyclin G1 protein.

The antibody is administered to the host such that the antibody or fragment or derivative thereof enters the cells of the site of the invasive vascular procedure or vascular lesion. Preferably, the antibody or fragment or derivative thereof which recognizes cyclin G1 protein is administered by transducing cells at the site of the invasive vascular procedure or of a vascular lesion with a polynucleotide encoding the antibody or fragment or derivative thereof which recognizes cyclin G1 protein. The polynucleotide may be contained in an appropriate expression vehicle such as those hereinabove described. In one embodiment, the expression vehicle is a retroviral vector as hereinabove described, which may be administered in an amount as hereinabove described. Such vector is administered intravascularly as hereinabove described, and may be administered directly to the site of an invasive vascular procedure or vascular lesion.

This method is applicable to the prevention and treatment of restenosis and the prevention or treatment of vascular lesions following a variety of invasive vascular procedures, including but not limited to, cardiovascular angioplasty, arterial grafts, and coronary bypass surgery. This method also applies to the prevention and treatment of vascular lesions including, but not limited to, lesions of the femoral, carotid, or renal arteries, particularly renal arteries associated with renal dialysis fistulas.

In accordance with another aspect of the present invention, there is provided a method of immortalizing non-tumor cells which comprises transducing the non-tumor cells with a polynucleotide encoding cyclin G1 protein or a derivative or analogue thereof. The term "derivative or analogue thereof" as used herein means that the protein may be a protein which has deletions and/or substitutions of amino acid residues with respect to the native cyclin G1 protein sequence, yet retains the same biological properties as native, or unmodified cyclin G1 protein. Although the scope of this aspect of the present invention is not intended to be limited to any theoretical reasoning, Applicants have discovered that overexpression of cyclin G1 protein in non-tumor cells, would contribute to cell immortalization and permanent cell lines that would retain the ability to respond to subsequent cell cycle events, and avoiding the use of viral oncogenes which cause cell transformation.

The polynucleotide encoding cyclin G1 protein or a fragment or derivative thereof may be contained in an appropriate expression vehicle, which may be as hereinabove described. In one embodiment, the expression vehicle is a retroviral vector, which may be as hereinabove described.

Non-tumor cells which may be transduced in accordance with this aspect of the present invention include, but are not limited to, fibroblasts, hepatocytes, muscle cells, endothelial cells, and epithelial cells.

In accordance with yet another aspect of the present invention, there is provided a method of enhancing transduction of cells with a retroviral vector. The method comprises transducing the cells with a first expression vehicle including a polynucleotide encoding cyclin G1 protein. The first expression vehicle is not a retroviral vector. The cells also are transduced with a second expression vehicle which preferably includes a polynucleotide encoding a therapeutic agent. The second expression vehicle is a retroviral vector. This method can be used to transduce cells in vivo or ex vivo or in vitro.

The first expression vehicle may be any expression vehicle which is not a retroviral vector. Such expression vehicles include, but are not limited to, plasmid vectors, eukaryotic vectors, prokaryotic vectors (such as, for example, bacterial vectors), and viral vectors other than retroviral vectors, including, but not limited to, adenoviral vectors, adeno-associated virus vectors, Herpes virus vectors, and vaccinia virus vectors.

In a preferred embodiment, the first expression vehicle is an adenoviral vector. Although this embodiment is not to be limited to any theoretical reasoning, cyclin G1 protein is induced in very early G1 phase, when cell activation occurs. The transduction of the cells with an adenoviral vector including a polynucleotide encoding cyclin G1 protein provides transient overexpression of cyclin G1 protein in the cells, thereby activating the cells, and enabling increased integration of the retroviral vector including the polynucleotide encoding the therapeutic agent into the cells. Such method is applicable particularly to the introduction of retroviral vectors into cells with low replication indices and low transduction efficiency.

The adenoviral vector which is employed may, in one embodiment, be an adenoviral vector which includes essentially the complete adenoviral genome (Shenk et al., *Curr. Top. Microbiol. Immunol.*, 111(3): 1-39 (1984). Alternatively, the adenoviral vector may be a modified adenoviral vector in which at least a portion of the adenoviral genome has been deleted.

In the preferred embodiment, the adenoviral vector comprises an adenoviral 5' ITR; an adenoviral 3' ITR; an adenoviral encapsidation signal; a DNA sequence encoding cyclin G1 protein; and a promoter controlling the DNA sequence encoding cyclin G1 protein. The vector is free of at least the majority of adenoviral E1 and E3 DNA sequences, but is not free of all of the E2 and E4 DNA sequences, and DNA sequences encoding adenoviral proteins promoted by the adenoviral major late promoter.

In one embodiment, the vector also is free of at least a portion of at least one DNA sequence selected from the group consisting of the E2 and E4 DNA sequences.

In another embodiment, the vector is free of at least the majority of the adenoviral E1 and E3 DNA sequences, and is free of a portion of the other of the E2 and E4 DNA sequences.

In still another embodiment, the gene in the E2a region that encodes the 72 kilodalton binding protein is mutated to produce a temperature sensitive protein that is active at 32° C., the temperature at which the viral particles are produced. This temperature sensitive mutant is described in Ensinger et al., *J. Virology*, 10:328-339 (1972), Van der Vliet et al., *J. Virology*, 15:348-354 (1975), and Friefeld et al., *Virology*, 124:380-389 (1983).

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site (which may be as herein described); a poly A signal; and a DNA segment which corresponds to a segment of the adenoviral genome. The vector also may contain a tripartite leader sequence. The DNA segment corresponding to the adenoviral genome serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAvS6, which is described in published PCT Application Nos. WO94/23582, published Oct. 27, 1994, and WO95/09654, published Apr. 13, 1995. The DNA sequence encoding cyclin G1 protein may then be inserted into the multiple cloning site to produce a plasmid vector.

This construct is then used to produce an adenoviral vector. Homologous recombination is effected with a modified or mutated adenovirus in which at least the majority of the E1 and E3 adenoviral DNA sequences have been deleted. Such homologous recombination may be effected through co-transfection of the plasmid vector and the modified adenovirus into a helper cell line, such as 293 cells, by $CaPO_4$ precipitation. Upon such homologous recombination, a recombinant adenoviral vector is formed that includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 (ATCC VR-5) genome.

Through such homologous recombination, a vector is formed which includes an adenoviral 5' ITR, an adenoviral encapsidation signal; an E1a enhancer sequence; a promoter; a DNA sequence encoding cyclin G1 protein protein; a poly A signal; adenoviral DNA free of at least the majority of the E1 and E3 adenoviral DNA sequences; and an adenoviral 3' ITR. The vector also may include a tripartite leader sequence. The vector may then be transfected into a helper cell line, such as the 293 helper cell line (ATCC No. CRL1573), which will include the E1a and E1b DNA sequences, which are necessary for viral replication, and to generate adenoviral particles. Transfection may take place by electroporation, calcium phosphate precipitation, microinjection, or through proteoliposomes.

The vector hereinabove described may include a multiple cloning site to facilitate the insertion of the DNA sequence encoding the cyclin G1 protein into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence encoding cyclin G1 protein into the cloning vector.

The DNA sequence encoding cyclin G1 protein is under the control of a suitable promoter, which may be selected from those herein described, or such DNA may be under the control of its own native promoter.

In one embodiment, the adenovirus may be constructed by using a yeast artificial chromosome (or YAC) containing an adenoviral genome according to the method described in Ketner, et al., *PNAS*, Vol. 91, pgs. 6186-6190 (1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence encoding cyclin G1 protein then may be cloned into the adenoviral DNA. The modified adenoviral genome then is excised from the adenovirus yeast artificial chromosome in order to be used to generate adenoviral vector particles as hereinabove described.

The retroviral vector, which is the second expression vehicle, may be as hereinabove described. Such retroviral vector includes a polynucleotide encoding a therapeutic agent. The term "therapeutic" is used in a generic sense and includes treating agents, prophylactic agents, and replacement agents.

Polynucleotides encoding therapeutic agents which may be contained in the retroviral plasmid vector include, but are not limited to, polynucleotides encoding tumor necrosis factor (TNF) genes, such as TNF-α; genes encoding interferons such as Interferon-α, Interferon-β, and Interferon-γ, genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; cytochrome b; glucocerebrosidase; T-cell receptors; the LDL receptor, ApoE, ApoC, ApoAI and other genes involved in cholesterol transport and metabolism; the alpha-1 antitrypsin (α1AT) gene; the insulin gene; the hypoxanthine phosphoribosyl transferase gene; the CFTR gene; negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthetase; vasoactive peptides; angiogenic peptides; the dopamine gene; the dystrophin gene; the β-globin gene; the α-globin gene; the HbA gene; protooncogenes such as the ras, src, and bcl genes; tumor-suppressor genes such as p53 and Rb; the LDL receptor; the heregulin-α protein gene, for treating breast, ovarian, gastric and endometrial cancers; monoclonal antibodies specific to epitopes contained within the β-chain of a T-cell antigen receptor; the multi-drug resistance (MDR) gene; polynucleotides encoding ribozymes; antisense polynucleotides; genes encoding secretory peptides which act as competitive inhibitors of angiotensin converting enzyme, of vascular smooth muscle calcium channels, or of adrenergic receptors, and polynucleotides encoding enzymes which break down amyloid plaques within the central nervous system. It is to be understood, however, that the scope of the present invention is not to be limited to any particular therapeutic agent.

The polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex thymidine kinase promoter; retroviral LTRs; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

The first expression vehicle, which preferably is an adenoviral vector, which includes a DNA sequence encoding cyclin G1 protein or an analogue derivative thereof, and the retroviral vector, which includes a polynucleotide encoding therapeutic agent, may transduce cells in vivo or in vitro.

In one embodiment the cells are transduced with the first expression vehicle, which preferably is an adenoviral vector, prior to transduction of the cells with the second expression vehicle (i.e., the retroviral vector). In another embodiment, the cells are transduced with the first expression vehicle and the second expression vehicle concurrently.

When administered in vivo, the adenoviral vector is administered in an amount effective to transduce the desired cells with the polynucleotide encoding cyclin G1 protein. The adenoviral vector may be administered systemically, such as, for example, by intravenous, intraarterial, or intraperitoneal administration. Alternatively, the adenoviral vector may be administered by direct, nonsystemic injection to a desired tissue, organ, or mass of cells, such as, for example, a tumor. In general, the adenoviral vector is administered at a multiplicity of infection of from about 1 to about 10.

The retroviral vector is administered to the animal host in vivo in an amount effective to produce a therapeutic effect in the animal.

The animal may be a mammal, including human and non-human primates. The retroviral vectors may be administered systemically, for example, intravenously or intraarterially or intraperitoneally, or by direct nonsystemic injection into a desired tissue, organ or mass of cells, such as, for example, a tumor.

The retroviral vectors are administered to an animal in an amount effective to produce a therapeutic effect in the animal. In general, the retroviral vectors are administered in an amount of at least $1 \times 10^5$ cfu/ml, and in general such amount does not exceed $1 \times 10^9$ cfu/ml. Preferably, the retroviral vectors are administered in an amount of from about $1 \times 10^6$ cfu/ml to about 1×10⁸ cfu/ml. The exact dosage to be administered is dependent upon various factors, including the age, height, weight, and sex of the patient, the disorder being treated, and the severity thereof.

The retroviral vectors and the adenoviral vectors each are administered to the patient in a pharmaceutically acceptable carrier, such as, for example, a physiological saline solution. Other pharmaceutical carriers include, but are not limited to, mineral oil, alum, and lipid vesicles such as liposomes. The selection of a suitable pharmaceutical carrier is deemed to be within the scope of those skilled in the art from the teachings contained herein.

In one embodiment, the eukaryotic cells which are transduced in vivo with the retroviral and adenoviral vectors are primary human cells. The gene encoding a therapeutic agent can be any gene having clinical usefulness, for example, therapeutic or marker genes. Preferably, the primary human cells are blood cells. The term "blood cells" as used herein is meant to include all forms of nucleated blood cells as well as progenitors and precursors thereof.

The gene carried by the blood cells can be any gene which directly enhances the therapeutic effects of the blood cells. The gene carried by the blood cells can be any gene which allows the blood cells to exert a therapeutic effect that it would not ordinarily have, such as a gene encoding a clotting factor (e.g., Factor VIII or Factor IX) useful in the treatment of hemophilia. The gene can encode one or more products having therapeutic effects. Examples of suitable genes include those that encode cytokines such as TNF, interleukins (interleukins 1-12), interferons (α, β, γ-interferons), T-cell receptor proteins and Fc receptors for binding to antibodies.

The retroviral vectors are useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, and other illnesses such as growth disorders and heart diseases, for example, those caused by alterations in the way cholesterol is metabolized and defects of the immune system.

In one embodiment, the retroviral vectors may include a negative selectable marker, such as, for example, a viral thymidine kinase gene, and more particularly, the Herpes Simplex Virus thymidine kinase (TK) gene. Such retroviral vectors may be administered in conjunction with the adenoviral vectors hereinabove described to tumor cells (in particular to cancer cells) in a human patient in vivo. The adenoviral vectors and the retroviral vectors then transduce the tumor cells. After the retroviral vectors have transduced the tumor cells, the patient is given an interaction agent, such as gancyclovir or acyclovir, which interacts with the protein expressed by the negative selectable marker in order to kill all replicating cells (i.e., the tumor cells) which were transduced with the retroviral vector including the negative selectable marker.

The adenoviral vectors and the retroviral vectors mentioned hereinabove also may be administered in an animal model for determining the effectiveness of a gene therapy treatment. For example, an adenoviral vector including a polynucleotide encoding cyclin G1 protein and a retroviral vector including a polynucleotide encoding a therapeutic agent, may be administered to animals of the same species. The retroviral vector is administered to the animals in varying amounts. From determining the effectiveness of the gene therapy treatment in the animal, one may determine an effective amount of the retroviral vector to be administered to a human patient.

In another embodiment, the adenoviral vectors, which include a DNA sequence encoding cyclin G1 protein, are administered in vivo to a patient in conjunction with retroviral producer cells which generate retroviral vectors including a polynucleotide encoding a therapeutic agent.

Such an embodiment is applicable particularly to the treatment of tumors (including malignant and non-malignant tumors) such as, for example, liver tumors, bone tumors, and lung tumors. For example, the producer cells may include a retroviral plasmid vector including a negative selectable marker. The adenoviral vectors and the retroviral producer cells then are administered to the tumor, whereby the producer cells generate retroviral vector particles including the polynucleotide encoding the negative selectable marker. The adenoviral vectors and the retroviral vector particles generated by the retroviral producer cells transduce the tumor cells, whereby the tumor cells produce the negative selectable marker. Upon administration of an interaction agent to the patient, the transduced tumor cells are killed.

Alternatively, the adenoviral vectors and the retroviral vector may transduce eukaryotic cells, in vitro, whereby the eukaryotic cells are cultured in vitro for the in vitro production of the therapeutic agent, or, alternatively, the transduced eukaryotic cells may be administered to a host as part of a gene therapy procedure, whereby the transduced eukaryotic cells express the therapeutic agent in vivo in a host.

As stated hereinabove, the above methods of the present invention may be accomplished through the use of appropriate expression vehicles containing either a polynucleotide encoding an agent which inhibits cyclin G1 protein (when one desires to treat a tumor by inhibiting cyclin G1 protein), or a polynucleotide encoding cyclin G1 protein (when one desires to immortalize a cell line or enhance retroviral transduction of cells). Thus, in accordance with another aspect of the present invention, there is provided an expression vehicle which includes a polynucleotide encoding an agent which, in one embodiment, is an agent which inhibits cyclin G1 protein. Such agents include those hereinabove described, such as, for example, antisense polynucleotides or antibodies or fragments or derivatives thereof which recognize cyclin G1 protein, or a cyclin-dependent kinase inhibitor. In another embodiment, the polynucleotide encodes cyclin G1 protein.

The expression vehicle may be selected from those hereinabove described, and preferably may be a viral vector, including RNA virus vectors and DNA virus vectors as hereinabove described.

In one embodiment, the viral vector is an RNA virus vector, and preferably is a retroviral vector, such as those hereinabove described. In another embodiment, the viral vector is a DNA virus vector, and preferably is an adenoviral vector, such as those hereinabove described.

In accordance with a further aspect of the present invention, there is provided a method of detecting cancer by detection of increased expression of cyclin G1 protein, with such increased expression being detected by detecting increased amounts of polynucleotides encoding cyclin G1 protein, or by detecting increased amounts of cyclin G1 protein, as compared with normal, non-cancerous cells. The method comprises contacting cells with an agent which binds to (i) cyclin G1 protein and/or (ii) a polynucleotide encoding cyclin G1 protein. Binding of the agent to cyclin G1 protein and/or a polynucleotide encoding cyclin G1 protein then is determined.

The cyclin G1 protein is expressed intracellularly, and to assay for the increased expression of cyclin G1 protein, appropriate procedures are employed prior to contacting the cells with agent which binds to cyclin G1 protein and/or a polynucleotide encoding cyclin G1 protein, to enable binding of the agent in the assay. Such procedures include, but are not limited to, the fixation of a histological sample of cells prior to the assay.

Agents which may be employed in this aspect include, but are not limited to, polynucleotides (e.g., DNA or RNA probes) which hybridize to a polynucleotide encoding cyclin G1 protein, and antibodies or fragments or derivatives thereof which recognize cyclin G1 protein.

In one embodiment, the agent is a polynucleotide which hybridizes to a polynucleotide encoding cyclin G1 protein.

In another embodiment, the agent is an antibody or fragment or derivative thereof which recognizes cyclin G3 protein. Such antibodies include, but are not limited to, monoclonal antibodies, polyclonal antibodies, and single chain antibodies.

Certain properties of cancer may be determined through the analysis of the amount of binding to cyclin G1 protein expressed in the cells, or the amount of binding to a polynucleotide encoding cyclin G1 protein present in the cells. A determination an elevated amount of binding of the agent to cyclin G1 protein as compared to that observed in normal cells, or to a polynucleotide encoding cyclin G1 protein may be indicative of the presence of cancer cells. Cancers which may be determined in accordance with this method include osteogenic sarcoma and Ewing's sarcoma, and other neoplastic disorders in which cyclin G1 is expressed, such as those hereinabove described.

The determination of binding of the agent to cyclin G1 protein or to a polynucleotide encoding cyclin G1 protein may be determined by a variety of assay methods known to those skilled in the art. Such assays include, but are not limited to, direct and indirect sandwich assays, colorimetric assays and ELISA assays.

In the above assays, the agent which binds to the cyclin G1 protein or to the polynucleotide which encodes cyclin G1 protein, or a binder which binds to the agent when an indirect sandwich assay is employed, is coupled to a detectable label or marker. Such labels or markers include, but are not limited to, radioactive isotopes of, for example, iodine, cobalt or tritium; an enzyme; a fluorescent dye; an absorbing dye; a chemiluminiscent substance; a spin label; biotin; hematoxylin; a colored particle or any other labeling substance known to one skilled in the art.

In one embodiment, fixed cells, suspected of being cancer cells, are contacted with an antibody which recognizes cyclin G1 protein. Detection of bound antibody may be determined by an indirect sandwich assay employing a biotin-avidin complex, such as a biotin-streptavidin complex which is bound to the antibody. The avidin is bound to an enzyme, such as, for example, alkaline phosphatase. The sample is contacted with a substrate for the enzyme, which produces a colored reaction product. By measuring the development of the colored reaction product, the amount of cyclin G1 protein in the sample of cells may be determined, thereby determining the presence of cancer and/or the extent and severity thereof.

EXAMPLES

The invention now will be described with respect to the following examples, however, the scope of the present invention is not intended to be limited thereby.

Example 1

Materials and Methods

Cloning of antisense cyclin G1, antisense cyclin D1, and p21/WAF1/CIP1 Expression Constructs.

The full coding regions of human cyclin G1 (FIG. 1) (Wu, et al., Oncol. Reports, Vol. 1, pgs. 705-711 (1994)), cyclin D1 (Xiong, et al., Cell, Vol. 65, pgs. 691-699 (1991)), and p21/WAF1/CIP1 (Harper, et al., Mol. Biol. Cell., Vol. 6, pgs. 387-400 (1995); El-Deiry, et al., Cell, Vol. 75, pgs. 817-825 (1993)), including the stop codons, were prepared by primer-directed RT-PCR amplification. To create the antisense cyclin G1 (aG1) expression construct, the 586 bp N-terminal fragment, including −65 bp of the untranslated region, was released by double digestion with XbaI/HpaI from the CYCG1 gene originally isolated from a human WI-38 fibroblast (ATCC, Rockville, Md.) cDNA library, and then cloned by blunt ligation into the pcDNA3 vector (Invitrogen, San Diego, Calif.) at the EcoRV site. The 605 N-terminal region of cyclin D1 (antisense orientation, aD1) and the 495 bp full coding region of WAF1/CIP1 (p21) were released by digestion with NdeI/NcoI and NdeI/EcoRI, respectively, followed by blunt end cloning into the pcDNA3 vector at the EcoRV site. The structure of each construct was confirmed by manual DNA sequence analysis, using a modified dideoxy chain termination method (United States Biochemicals).

Construction of Retroviral Vectors Bearing Cell Cycle Control Genes (G1aG1SvNa, G1aD1SvNa, and G1p21SvNa: Retroviral Vector Source, pG1XSvNa; Insert Source, pcDNA3aG1, pcDNA3aD1, pcDNA3p21).

To create each retroviral vector, pG1XSvNa (Genetic Therapy, Inc., Gaithersburg, Md.) was digested with NotI, the 5' phosphates were removed by treatment with calf intestinal alkaline phosphatase, and the resulting fragment was then gel-purified (1% agarose), excised, and electroeluted. pG1XSvNa is a retroviral plasmid vector derived from pG1 (described in PCT Application No. WO91/10728 published Jul. 25, 1991), and which includes a retroviral 5' LTR, a retroviral 3' LTR, a multiple cloning region and a neomycin resistance gene under control of the SV40 promoter. pG1XSvNa is described further in PCT Application No. WO95/09654, published Apr. 13, 1995. This procedure generated a 5856 bp long fragment of DNA which cannot relegate or re-circularize. To isolate the aG1, aD1 and p21 insert fragments, the respective plasmid DNAs were double digested with HindIII/NotI for aG6 and EcoRI/NotI for aD1 and p21, respectively. These digests were resolved on 1% agarose gels yielding the 597 bp HindIII/NotI fragment of aG1, the 632 bp EcoRI/NotI fragment of aD1, and the 522 bp EcoRI/NotI fragment of p21. These bands were then excised from the agarose gels and electroeluted. The NotI end of each insert was ligated to the NotI end of the digested pG1XSvNa vector, and isolated on 1% agarose gels yielding 6453, 6488 and 6378 bp long fragments for aG1, aD1 and p21 respectively. Each fragment was then electroeluted and treated with the Klenow fragment to generate blunt ends, and then ligated to generate closed plasmid DNA including the respective genes of interest. Successful cloning and insert orientation were determined by restriction analysis. The expected DNA fragments generated by digestion with BstEII and NotI were 920, 955 and 845 bp for aG1, aD1 and p21 inserts respectively, and .±0.5500 bp for the vector DNA.

Retroviral Vector Supernatants and Producer Cell Lines.

The β galactosidase and HStk expression vectors were kindly provided as high titer PA317 packaging cell clones (titers: $1.3 \times 10^6$ and $4.9 \times 10^6$ G418$^r$ colony-forming units, cfu/ ml for β galactosidase and HStk vectors respectively) by Genetic Therapy, Inc. (Gaithersburg, Md.). The 3 experimental retroviral plasmid vectors bearing cell cycle control enzyme cDNAs were packaged in PA317 cells (Miller, et al., *Mol. Cell Biol.*, Vol. 6, pgs. 2895-2902 (1986)) and tested as pooled vector supernatants (vector titer: 1×10$^6$ cfu/ml each). The vectors are referred to as G1BgSvNa, G1TK1SvNa.7, G1p21SvNa, G1aD1SvNa and G1aG1SvNa to indicate the order of promoters and coding regions contained in each vector (G1 vector, Moloney Murine Leukemia Virus long terminal repeat (LTR) sequences; Bg, β galactosidase or lacZ gene; HStk, Herpes Simplex thymidine kinase gene; aG1, antisense human cyclin G1; aD1, antisense cyclin D1; p21, Cdk inhibitor p21/Waf1/Cip1 gene; Sv, SV40 early region enhancer/promoter; and Na.7, neo$^r$ gene, clone 7). Retroviral vector G1TK1SvNa 7 is described further in PCT Application No. WO95/09654, published Apr. 13, 1995. Retroviral vector G1BgSvNa was generated from the plasmid pG1BgSvNa. pG1BgSvNa was constructed by digesting pSvNa (PCT Application No. WO95/09654) and pG1Bg (PCT Application No. WO91/10728) with SalI and HindIII. The SalI-HindIII fragment of pSvNa containing the SV40 promoter and a neomycin resistance gene was ligated to the SalI/HindIII digested pG1Bg to form pG1BgSvNa.

The vector source, G1XSvNa, containing only the SV40 promoter-driven neo$^r$ gene was used as a control for the effects of gene transduction and G418 selection.

Cells, Cell Culture Conditions and Transduction of Cells with lacZ, Cell Cycle Control Genes, and HStk Vectors.

Human osteogenic sarcoma (MG-63, ATCC No. CRL 1427) cells and primary normal diploid human fibroblasts (of hepatic origin) were cultured at a plating density of 2.5×10$^4$ cells in each of six-well plates, in DMEM supplemented with 10% FBS (D10). After overnight attachment, the cells were exposed to 1 ml of the respective retroviral vector in the presence of Polybrene (8 μg/ml) for 2 hours, after which 1 ml of fresh D10 was added to each well. Forty-eight hours after transduction with the lacZ vector, gene transfer efficiency was measured by determining the percentage of lacZ positive cells, upon X-gal staining and light microscopy.

Ganciclovir (GCV) Cytotoxicity/Bystander Effects in HStk Vector Transduced MG-63 Cells.

Initial dose-response studies determined the sensitivity of MG-63 cells and the optimal concentrations of G418 used to select transduced cells. Upon G418 selection, varying proportions of HStk-transduced and non-transduced MG-63 cells (plating density 2.5×10$^4$ cells) were exposed to 20 μg GCV/ml D10 in each of six-well plates, for 10 days. Hence, the bystander effects of GCV in HStk-transduced MG-63 were measured by determining the degree of confluency of cells in each well in 10 day cultures. Bystander effects of GCV treatment were compared to those in HStk-transduced NIH 3T3 cells (ATCC No. CRL 1658).

Evaluation of Cell Growth, Protein Expression, and Apoptosis in MG-63 Cells Bearing Chimeric Retroviral Vectors.

To assess the cytostatic effects of retroviral vectors bearing cell cycle modulators, the cells that were transduced with control vectors or vectors expressing cell cycle modulators were evaluated for their proliferative potential by counting the number of viable cells in each culture at serial intervals (0, 24, 48, 72, 144 and 192 hrs) after transduction. Western analysis of protein expression was performed as described previously (Williams, et al., *J. Biol. Chem.*, Vol. 268, pgs. 8871-8880 (1993); Wu, et al., *Oncol. Reports*, Vol. 2, pgs. 227-231 (1995)), using a polyclonal anti-peptide antibody recognizing the C-terminal 18 amino acids of human cyclin G1 (Wu, et al., 1994). To analyze the comparative efficacy of antisense G1, antisense D1, and p21 expression in the induction of apoptosis in MG-63 cells, the cells initially were examined by light microscopy for morphologic changes associated with apoptosis (cell shrinkage, cytolysis, nuclear fragmentation, and condensation of chromatin). The relative number of apoptotic cells were further confirmed and quantified using the Apoptag Plus in situ apoptosis detection kit (Oncor, Gaithersburg, Md.), which specifically detects the nascent 3'-OH DNA ends generated by endonuclease-mediated DNA fragmentation. The significance of differences among retroviral vectors bearing aG1, aD1, and p21 inserts, and control vectors was determined by analysis of variance.

Results

Hagen Osteogenic Sarcoma as a Target for Gene Therapy Using Retroviral Vectors.

Initial studies were aimed at characterizing the transduction efficiency of human osteosarcoma cells, using the G1BgSvNa retroviral vector construct. The apparent transduction efficiency of the retroviral vector was relatively high, approaching 80-90% for the transformed MG-63 cells, as compared to normal diploid fibroblasts in which transduction efficiencies of 20-30% were observed. FIG. 2 shows the β-galactoisidase staining MG-63 cells following transduction with the lacZ vector. Next, potential "bystander" cytocidal effects by mixing cells transduced with the Herpes Simplex thyrnidine kinase (HStk) gene with non-transduced cells followed by exposure to 20 μg/ml ganciclovir (GCV) was examined. FIG. 3 is a graph which shows the degree of confluency (%) in mixtures of HStk+ and HStk- MG-63 cells cultured for 10 days in the presence of GCV (20 μg/ml). The non-transduced cultures containing 100% HStk- cells showed 75% confluency. In contrast, the cultures containing 10% HStk+/ 90% HStk- and 30% HStk+/70% HStk- cells showed only 15% confluency, while cultures containing 50% HStk+/50% HStk- cells achieved 10% confluency, and cultures with greater than 50% HStk+ cell cultures achieved <10% confluency. The non-linearity of the survival curve demonstrates a significant bystander effect of GCV in mixed cultures of MG-63 cells. Both the high transduction efficiency of retroviral vectors and the occurrence of pronounced bystander effects to HStk+/GCV treatment attest to the feasibility of gene therapy for human osteogenic sarcoma using retroviral vectors.

Cytostatic and Cytocidal Effects of the Antisense Cyclin G1 Retroviral Vector in Cultured Human Osteogenic Sarcoma Cells.

Figure 5:
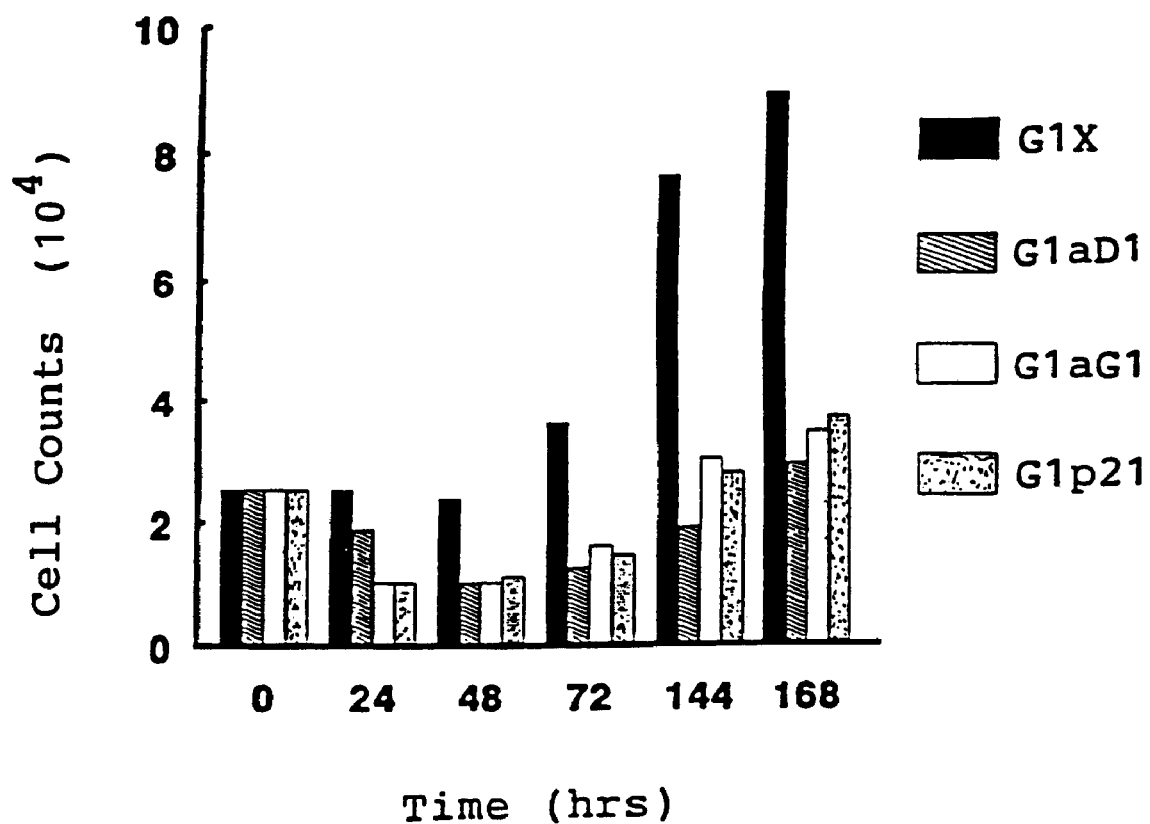
FIG. 5 is a graph of the cell counts in cultures of MG-63 cells transduced with G1XSvNa, G1aD1SvNa, G1aG1SvNa, or G1p21SvNa.

The structure of the experimental retroviral vector constructs are presented diagrammatically in FIG. 4, including the location of the neomycin phosphotransferase (neo$^r$) gene positioned downstream of the respective genes for 3 cell cycle control proteins, two of which are truncated fragments engineered in antisense orientation. The expected sizes of the transcripts for antisense cyclin G1, antisense cyclin D1, and p21 expression vectors are 3421, 3456, and 3346 base pairs, respectively. Transduction of MG-63 cells with each of the test vectors (FIG. 5) revealed a marked reduction in the number of viable cells observed at 24 to 168 hours post-transduction, when compared to transduced cultures containing the control vector expressing only the neo$^r$ gene. Cell densities were measured, by cell counting, in cultures of MG-63 cells at serial intervals after transduction with the retroviral vectors bearing antisense cyclin G1 (G1aG1), antisense cyclin D1 (G1aD1), and p21(G1p21), as well as the control vector G1XSvNa (G1X).

As shown in FIG. 6, the comparative expression of the p29 cyclin G1 protein was analyzed by Western blotting, and found to be significantly reduced in MG-63 cells bearing the antisense cyclin G1 vector.

Antisense Knock-Out Cyclin G1 Induces Apoptosis in Human Osteogenic Sarcoma Cells.

Figure 7:
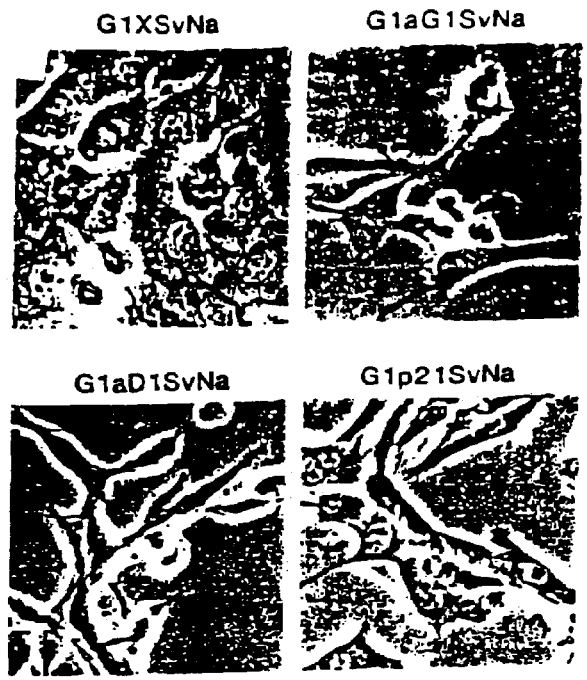
FIG. 7 depicts the morphological appearance of MG-63 cells by light microscopy at 72 hours after transduction of such cells with G1XSvNa, G1aG1SvNa, G1aD1SvNa, or G1p21SvNa.
Figure 8:
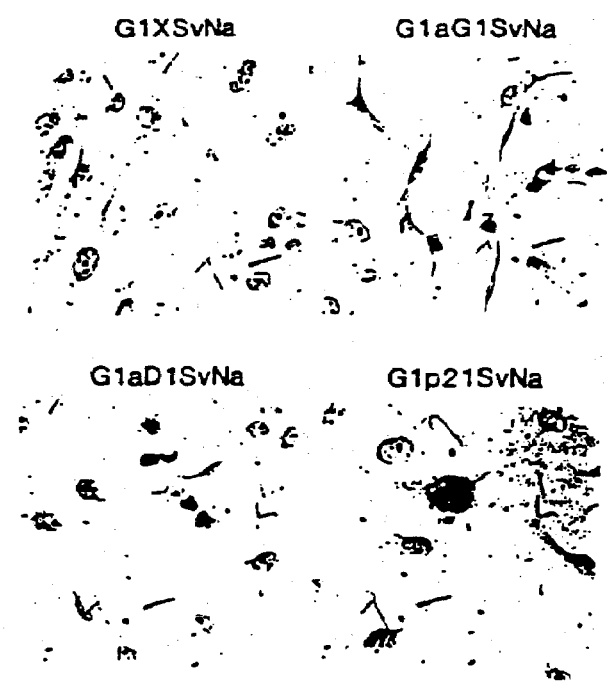
FIG. 8 depicts the detection of apoptotic cells in cultures of MG-63 cells transduced with G1XSvNa, G1aG1SvNa, G1aD1SvNa, or G1p21SvNa.

The morphological appearance of MG-63 cells was observed by light microscopy at 72 hours after transduction of retroviral vectors bearing antisense cyclin G1, antisense cyclin D1, p21 inhibitor, and control vector constructs (FIG. 7). In addition to significant decreases in cell densities observed in cultures transduced with vectors containing antisense cyclin G1, as well as the antisense cyclin D1 and p21 constructs (see FIG. 5), morphological evidence of apoptotic changes were noted, including cell shrinkage, nuclear segmentation, chromatin condensation, and nuclear fragmentation (Arends, et al., *Int. Rev. Exp. Pathol.*, Vol. 32, pgs. 223-254 (1991); Wyllie, et al., *International Review of Cytology*, Vol. 68, pgs. 251-306 (1980)), in cells transduced with each of these cell cycle control elements. To investigate further the mechanism of cell death, a molecular/immunocytochemical approach (Arends, et al., *Amer. J. Path.*, Vol. 136, pgs. 593-608 (1990); Gavrieli, et al., *J. Cell Biol.*, Vol. 119, pgs. 493-501 (1992)) was employed to detect the endonuclease-mediated DNA cleavage fragments that are characteristic of apoptosis (Bursch, et al., *Biochem. Cell Biol.*, Vol. 68, pgs. 1071-1074 (1990); Compton, *Canc. Metast.*, Vol. 11, pgs. 105-119 (1992)). FIG. 8 shows the detection of apoptotic cells by immunocytochemical analysis of DNA fragmentation in cultures bearing the chimeric vectors containing antisense cyclin G1, antisense cyclin D1, and p21 constructs. The induction of apoptosis in each of the cultures transduced with the cell cycle control vectors was determined to be highly significant (antisense cyclin G1, mean incidence=$38.8\pm5.0\%$, n=6, p<0.001; antisense cyclin D1, mean incidence=$37.4\pm24.4\%$, n=6, p<0.01; and p21, mean incidence=$37.5\pm8.2\%$, n=6; p<0.001) when compared to cultures transduced with the control vector (mean incidence=$3.6\pm4.1\%$, n=6). These results confirm that the observed cytocidal effects of these retroviral-mediated cell cycle blockades result from apoptosis.

Metastatic osteogenic sarcoma is a target for experimental gene therapies as it is invariably associated with a fatal outcome. This type of sarcoma tends to recur locally, spread to other bones or to lungs, which are surgically accessible sites. In fact, recent studies have reported increased survival time in patients who have undergone aggressive metastasectomy (Damron, et al., *Oncology*, Vol. 9, pgs. 327-340 (1995)). The safety and efficacy of therapeutic vectors bearing specific cell cycle control enzymes or HStk could be evaluated by intratumoral injection of producer cells or vector supernatant into metastatic foci, followed by metastasectomy and histologic examination for evidence of apoptosis, cytolysis or overt cytodifferentiation. The present study reveals a relatively high transduction efficiency of MG-63 osteosarcoma cells for the above-mentioned retroviral vectors in comparison with normal diploid fibroblasts. Interestingly, the apparent transduction efficiency of these cells (80-90%) is far greater than the percentage of cells in S phase in asynchronous cultures (Carbonaro-Hall, et al., *Oncogene*, Vol. 8, pgs. 1649-1659 (1993)). Non-transduced MG-63 cells exhibited significant "bystander" cytocidal effects of ganciclovir, when mixed with HStk+transduced cells, which, together with retroviral transduction susceptibility, affirm the feasibility of developing gene therapy approaches in the clinical management of metastatic disease.

Previous studies characterized the precise sequence of cyclin expression in MG-63 osteosarcoma cells (Wu, et al., *Int. J. Oncol.*, Vol. 3, pgs. 859-867 (1993); Carbanaro-Hall, 1993; Hall, et al., *Oncogene*, Vol. 8, pgs. 1377-1384 (1993); Williams, et al., *J. Biol. Chem.*, Vol. 268, pgs. 8871-8880 (1993)), enabling the temporal localization of a novel Cdk-associated cell cycle block point revealed by the antiproliferative agent rapamycin (Albers, et al., *J. Biol. Chem.*, Vol. 268, pgs. 22825-22829 (1993)). The results of the present study with retroviral vectors confirms the results of previous studies using penetrant antisense oligonucleotides (Wu, 1993): that antisense strategies directed against the cyclin D1 locus effectively inhibit osteosarcoma cell proliferation. The mechanism of cell death observed in cells transduced with each of the experimental constructs (i.e., aG1, aD1, and p21) was determined to be apoptosis, which is of considerable importance in terms of therapeutic efficacy in vivo.

The physiological function of cyclin G1 and its therapeutic potential is of particular interest, in that this candidate protooncogene (CYCG1) was first linked to cancer pathogenesis in human osteosarcomas (Wu, 1994). Moreover, a recent study suggests that cyclin G1, like p21, is a transcriptional target of the p53 tumor suppressor protein (Okamoto, et al., *EMBO J.*, Vol. 13, pgs. 4816-4822 (1994)). However, the initial hypothesis that cyclin G1 might counterintuitively function as an inhibitory subunit of cyclin-dependent kinases in a p53-mediated pathway to prevent tumorigenesis was discounted by experiments in which enforced overexpression of cyclin G1 failed to cause cell cyclin arrest in either normal or neoplastic cell lines (Okamoto, 1994). In contrast, the present study represents the first demonstration that cyclin G1 is essential for the survival and/or growth of osteosarcoma cells. These new data support the concept that cyclin G1 is involved in cell activation and or "competence" (Wu, 1994), and that blockade of cyclin G1 expression by antisense constructs exert profound cytocidal as well as cytostatic effects.

Example 2

Materials and Methods

Retroviral Vector Supernatants and Producer Cell Lines.

The β-galactosidase and p53 expression vectors were kindly provided as high titer PA317 packaging cell clones (titers: $1.3\times10^6$ and $2\times10^6$ colony-forming units, cfu/ml for β-galactosidase and p53 vectors, respectively) by Genetic Therapy, Inc. (Gaithersburg, Md.). The experimental vector bearing antisense cyclin G1 cDNA was packaged in PA317 cells and grown to high titer clones (vector titer: $1\times10^6$ cfu/ml each). The vectors are referred to as G1BgSvNa, G1p53SvNa.7, and G1aG1SvNa to indicate the order of promoters and coding regions contained in each vector (G1 vector, Moloney murine leukemia virus long terminal repeat (LTR) sequences; Bg, β-galactosidase or lacZ gene; p53, p53 tumor suppressor gene; aG1, antisense human cyclin G1; Sv, SV40 early region enhancer/promoter; and Na, $neo^r$ gene). The vector source, G1XSvNa, containing only the SV40 promoter-driven $neo^r$ gene was used as a control for the effects of gene transduction and G418 selection.

The vector G1p53SvNa.7 was constructed from pG1XSvNa and the plasmid pp53. Plasmid pp53 was constructed from pBSK-SN3, obtained from PharmaGenics (Allendale, N.J.), which contains a 1.8 kb XbaI fragment that includes the wild type p53 open reading frame as well as 5' and 3' untranslated regions cloned into the XbaI site of pBluescriptSK (Stratagene, LaJolla, Calif.). pBSK-SN3 was digested with SmaI and partially digested with NcoI to generate a 1,322 bp fragment containing the p53 open reading frame. The fragment was gel purified and ligated into plasmid pBg (described in published PCT Application No. WO91/10728, published Jul. 25, 1991), in place of the β-galactosidase gene between the NcoI and the XhoI sites to yield plasmid pp53.

Plasmid pG1XSvNa was digested with SnaBI and NotI. The SnaBI and NotI sites are located in the polylinker region of the plasmid. The digest generated a fragment having a length of 5,848 base pairs. The ends of the fragment were treated with calf intestinal alkaline phosphatase.

Plasmid pp53 was digested with NotI and SmaI, the digest generated a 2,081 base pair fragment and a 1,400 base pair fragment. The 1,400 base pair fragment contained the p53 gene. This fragment was isolated and gel purified.

The 5,848 base pair fragment obtained from pG1XSvNa, and the 1,400 base pair fragment obtained from pp53, with each fragment having sticky/blunt ends, were ligated to form pG1p53SvNa. The resulting plasmid was identified and confirmed by several diagnostic restriction analyses. The plasmid pG1p53SvNa then was packaged in PA317 cells to generate the retroviral vector G1p53SvNa.7.

Cells, Cell Culture Conditions and Transduction of Cells with lacZ, Antisense Cyclin G1 and p53 Vectors.

Rabbit undifferentiated carcinoma (VX2) cells and other primary and established cell lines were cultured at a plating density of $2.5 \times 10^4$ cells in each of six-well plates, in DMEM supplemented with 10% FBS (D10). After overnight attachment, the cells were exposed to 1 ml of the respective retroviral vector in the presence of Polybrene (8 μg/ml) for 2 hours, after which 1 ml of fresh D10 was added to each well. Forty-eight hours after transduction with the lacZ vector, gene transfer efficiency was measured by determining the percentage of lacZ positive cells, upon X-gal staining and light microscopy.

Evaluation of Cell Proliferation and Cell, Cycle Kinetics in VX2 Transduced with Retroviral Vectors Bearing Cell Cycle Control Genes.

To assess the cytostatic effects of retroviral vectors bearing cell cycle modulators, the cells that were transduced with control vectors, or vectors expressing antisense cyclin G1 or p53 genes, were evaluated for their proliferative potential by counting the number of viable cells in each culture at serial intervals after transduction. The effect of cell cycle modulators on the cell cycle kinetics of VX2 (carcinoma) as well as MG-63 (sarcoma) cells was tested by FACS analysis. The survival of transduced VX2 cells in the presence of G418 also was evaluated to determine to what extent the antisense cyclin G1 was cytocidal to the transduced cells.

Development of a Tumor Model in Athymic Nude Mice for in vivo Gene Therapy Using Retroviral Vectors Bearing Cell Cycle Modulators.

Undifferentiated carcinoma (VX2) tumors have been grown successfully in nude mice by subcutaneous implantation of VX2 cells. These tumors grow rapidly within three weeks, and are surgically accessible for evaluation of changes in tumor volume and morphology. Briefly, VX2 tumors were grown over 5 weeks in athymic nude mice by subcutaneous injection of $1 \times 10^7$ VX2 cells. When the tumors reached 100 mm$^3$ in size, 100 μl of concentrated retroviral vector supernatant (G1aG1SvNa, bearing the antisense cyclin G1 gene or the G1XSvNa control vector, bearing only the neo$^r$ gene: vector titer, $1 \times 10^8$ cfu/ml) was injected intratumorally, under Metofane anesthesia, every day for 2 weeks. Tumor volume was measured every week using a Vernier caliper, and the percentage change in tumor volume was estimated. The significance of differences between the antisense cyclin G1 vector- and control vector-treated tumors was tested using the Student's t test. Additionally, the formalin-fixed tumors were stained with hematoxylin-eosin (H & E) for histologic examination.

Results

A wide variety of cell lines were tested for sensitivity to retroviral vectors bearing cell cycle modulators. The results of such testing are given in Table I below.

TABLE I

In Vitro Transduction Efficiencies and Cytostatic Effects of an Antisense Cyclin G1 Retroviral Vector in Cancer and Non-cancer Cells

| Cell Line | Cell Type | Transduction Efficiency (G1BgSvNa) | Cytostatic Effect (GlaG1SvNa) |
|---|---|---|---|
| Human Cancer | | | |
| MG-63 | osteosarcoma | 80% | + |
| HT29 | colon carcinoma | 13% | + |
| Bxpc-3 | pancreatic carcinoma | 9% | + |
| Miapaca | pancreatic carcinoma | 19% | + |
| Mnng/Hos | osteosarcoma | 15% | + |
| EW-1 | Ewing's Sarcoma | 5% | + |
| MDA-MB 231 | breast cancer | <1% | − |
| Non-human Cancer | | | |
| XC-6 (rat) | osteosarcoma | 22% | + |
| Km12C (rat) | colon carcinoma | 20% | + |
| Km12C4A (rat) | colon carcinoma | 15% | + |
| Km12SM (rat) | colon carcinoma | 15% | + |
| C6 (rat) | glioma | 5% | + |
| VX-2 (rabbit) | undifferentiated CA | 6% | + |
| Human Non-cancer | | | |
| primary | bone marrow stroma | 22% | − |
| primary | activated keratocyte | 20% | + |
| primary | hepatic fibroblast | 23% | − |
| primary | keloid fibroblast | 31% | + |
| primary | dermal fibroblast | 24% | + |
| ECU | endothelial | 5% | − |
| Non-human Non-cancer | | | |
| A10 (rat) | aortic smooth muscle | 45% | + |
| NIH3T3 (mouse) | fibroblast | 30% | + |

Of the cells tested, proliferation of 4 colon cancer cells (HT-29, KM12C4A, KM12C and KM12SM), Ewings sarcoma (EW-1), C6 glioma, 2 pancreatic cancer (BxPc3, Miapaca) and 2 osteosarcoma (MG-63, MnngHOS) was inhibited by the antisense cyclin G1 retroviral vector. The HT29, BxPc3, and KM12SM cells were also sensitive to wild type p53. Among the non-cancer cell lines, cytostasis was induced by antisense cyclin G1 and p53 in embryonic rat aortic smooth muscle cells and human skin and keloid fibroblasts, but not in normal human stromal, human liver-derived fibroblasts or human endothelial cells.

Figure 9A:
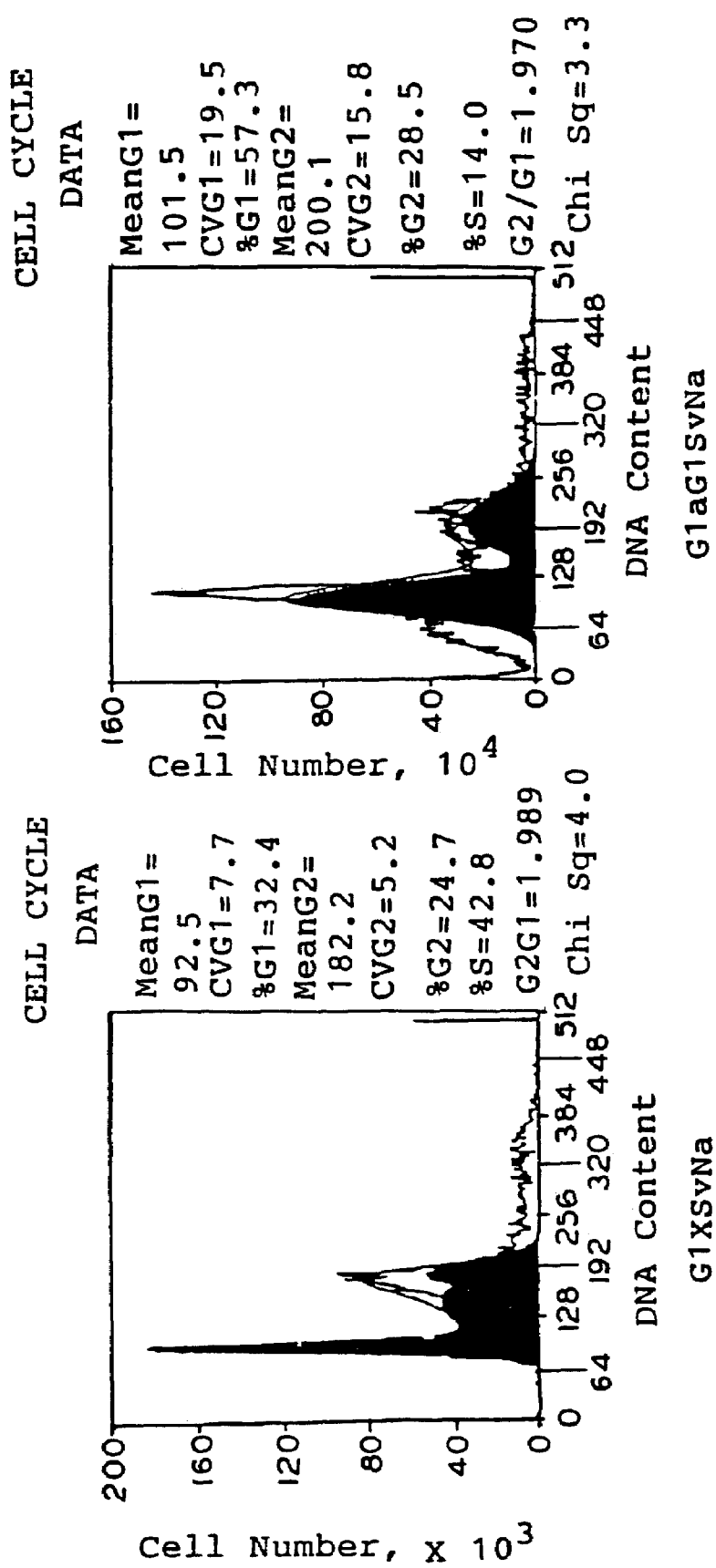
FIG. 9A depicts FACS analysis of PI-stained nuclei 48 hours after transduction of VX2 carcinoma cells with a retroviral vector bearing antisense cyclin G1 (G1aG1SvNa), compared with that of the control (G1XSvNa) vector.
Figure 9B:
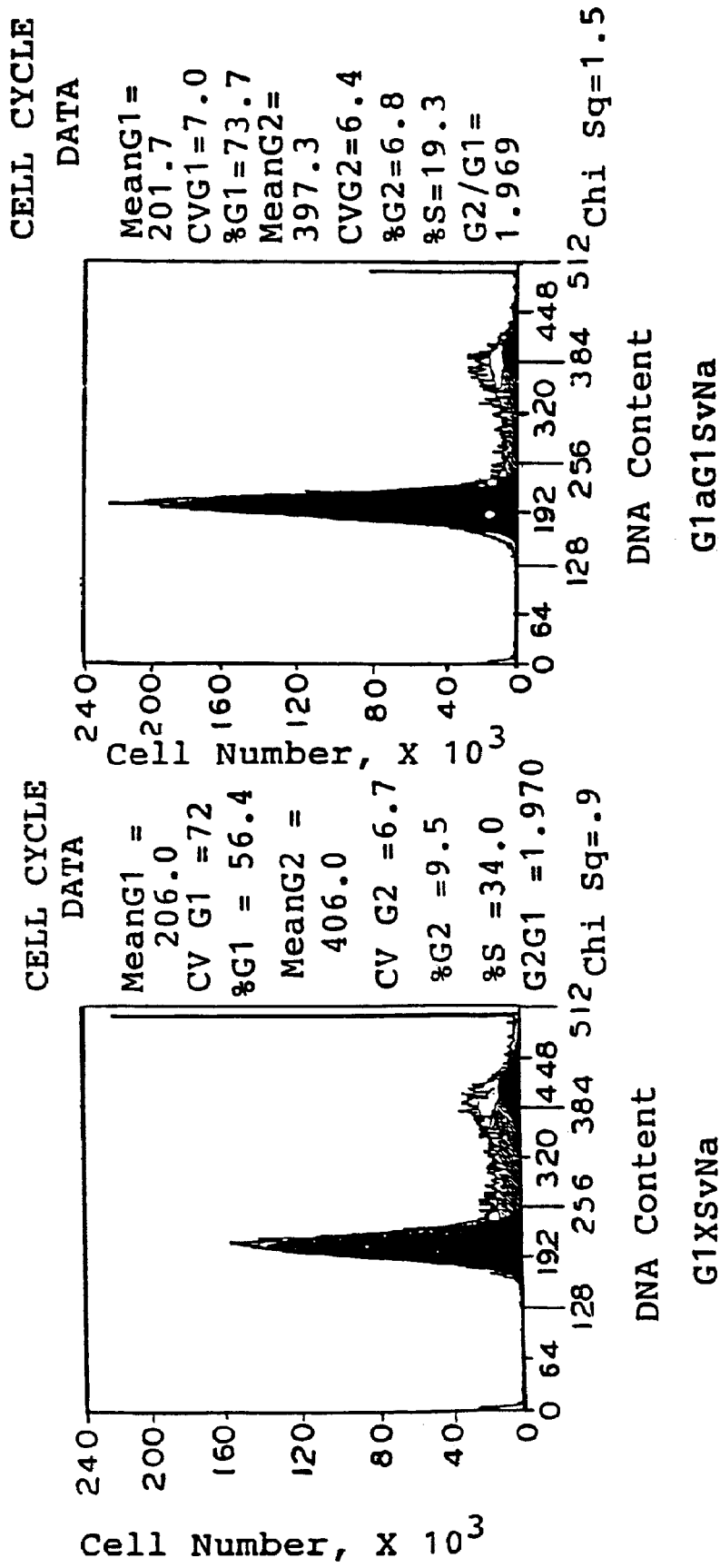
FIG. 9B depicts FACS analysis of PI-stained nuclei 48 hours after transduction of MG-63 osteosarcoma cells with retroviral vectors bearing antisense cyclin G1 (G1aG1SvNa) compared with the control (G1XSvNa) vector.

FACS analysis was used to investigate the effect of the antisense cyclin G1 retroviral vector on the cell cycle kinetics of sarcomatous and carcinomatous tumor cells. VX2 undifferentiated carcinoma cells transduced with retroviral vectors bearing antisense cyclin G1 showed profound alterations of cell cycle kinetics upon FACS analysis, exhibiting a broadening of peaks that is indicative of nuclear fragmentation and a reduction of cells in S phase (FIG. 9A). In comparison, FACS analysis of MG-63 cells transduced with the antisense cyclin G1 vector showed accumulation of cells in G1 phase, and a significant decrease in the number of cells in S phase, suggesting that the mechanism of cytostasis in these transduced cells accompanies a G1 phase cell cycle block (FIG. 9B).

Figure 10:
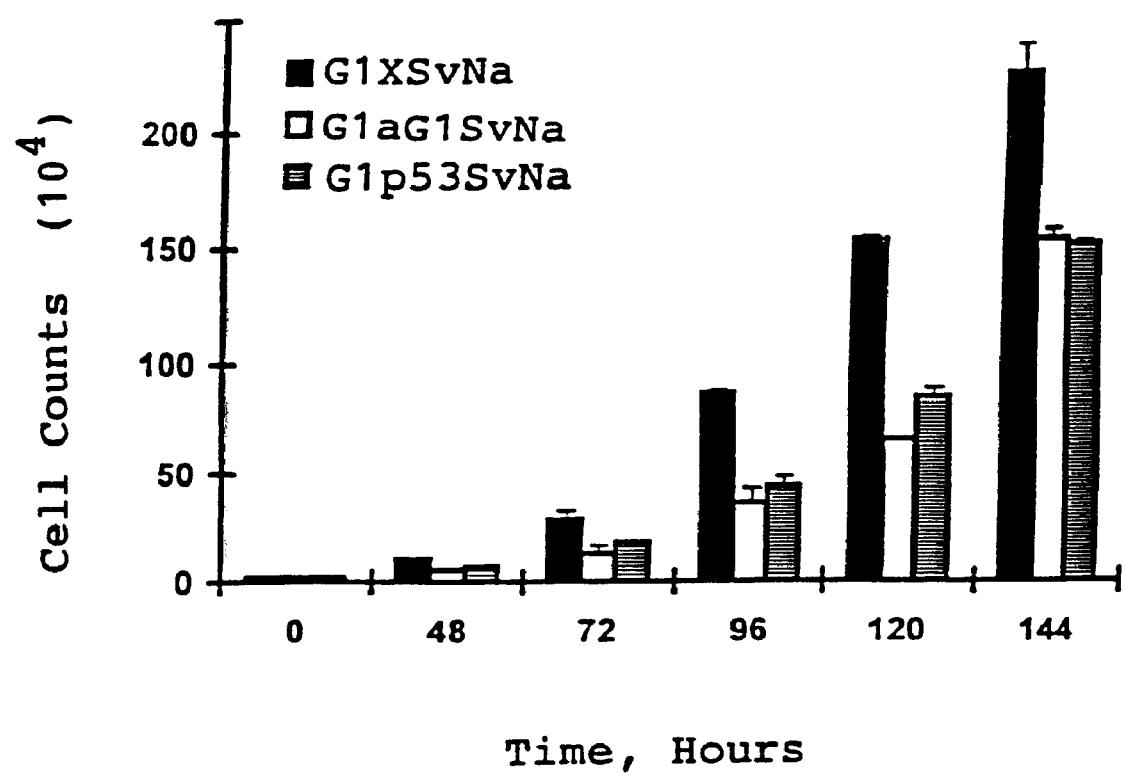
FIG. 10: Cytostatic effects of retroviral vectors bearing antisense cyclin G1 and wild type p53 in transduced VX2 undifferentiated carcinoma cells. Cell densities were measured, by cell counting, in cell cultures of VX2 cells at serial intervals after retroviral vector transduction prior to G418 selection.
Figure 11:
FIG. 11: Morphological appearance of VX2 cells 10 days after transduction with retroviral vectors bearing antisense cyclin G1 (G1aG1SvNa), wild type p53 (G1p53SvNa) or the control (G1XSvNa) vector after G418 selection.

Simultaneous with the altered cell cycle kinetics, the antisense cyclin G1 as well as the p53 vectors inhibited proliferation of VX2 carcinoma cells over 144 hours compared with control vector-treated cells (FIG. 10). Upon selection of transduced cells with G418, only 5% of the VX2 cells were eliminated (FIG. 11), indicating that the vast majority of cells bearing antisense cyclin G1 and wild type p53 had undergone cell death, presumably via apoptosis. These data represent the first in vitro demonstration that antisense cyclin G1 may exhibit antitumor activity in cancers of epithelial origin.

Figure 12:
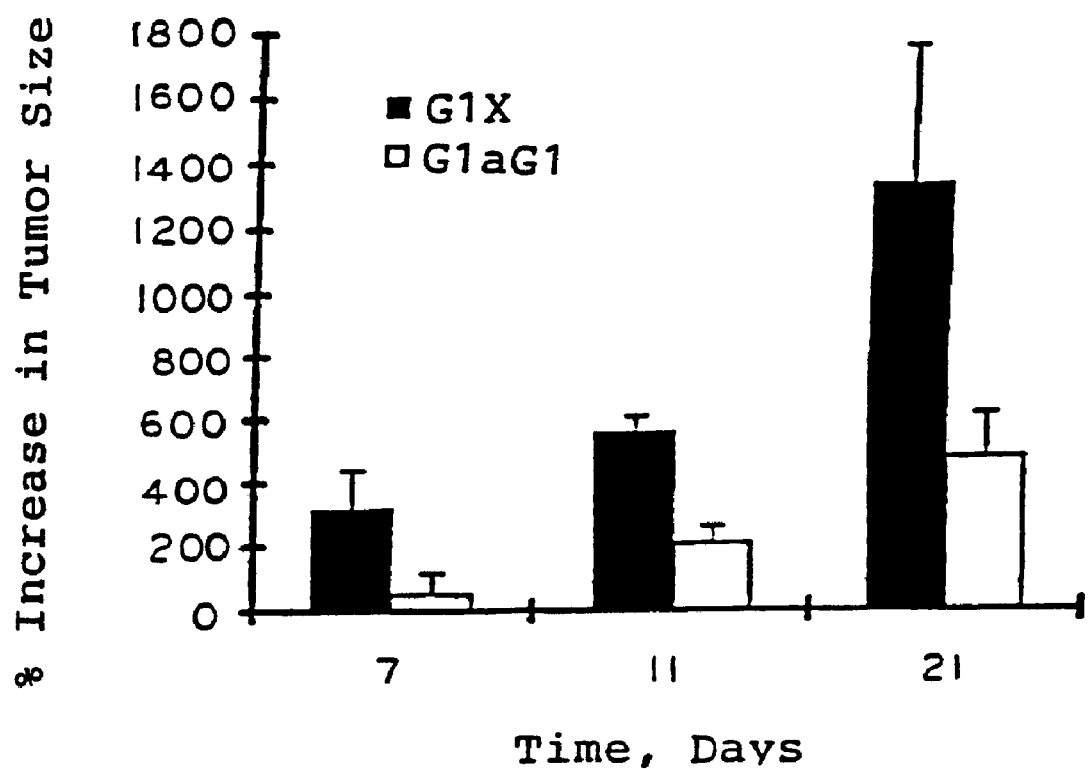
FIG. 12: Inhibition of VX2 tumor growth in nude mice following intratumoral injection retroviral vector bearing antisense cyclin G1. The percentage increase in tumor size, plotted on the vertical axis, is expressed as a function of time (days), plotted on the horizontal axis.

FIG. 12 shows inhibition of VX2 tumor growth in nude mice by intratumoral, injection of a retroviral vector bearing antisense cyclin G1 (G1aG1) when compared to growth of VX2 tumors in mice receiving the control vector (G1X; p<0.05 at 7 days; p<0.001 at 11 days; and p<0.05 at 21 days; n=3 mice each group). In 1 of 5 mice treated with antisense cyclin G1 vector, a 12% decrease in tumor size was noted one week following treatment. In contrast, tumor growth was not arrested in the mice treated with the control vector.

Figure 13A:
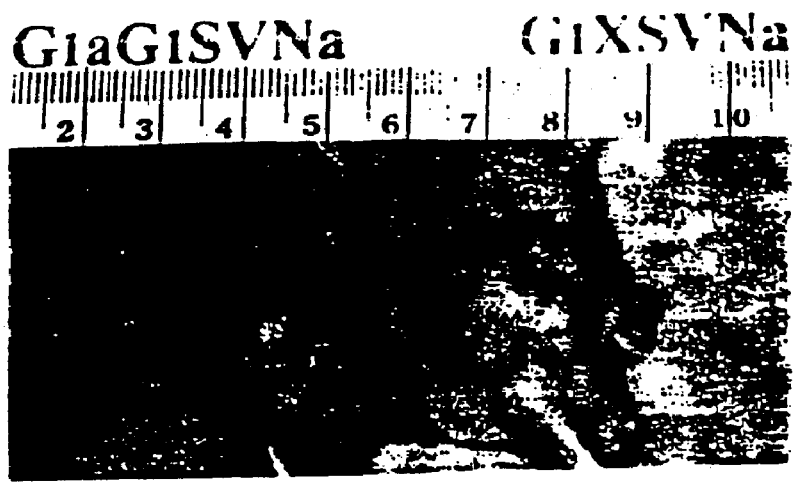
FIG. 13A: Gross appearance of representative VX2 tumor-bearing mice one week after treatment with retroviral vectors bearing antisense cyclin G1 (G1aG1SvNa) or the control vector (G1XSvNa).
Figure 13B:
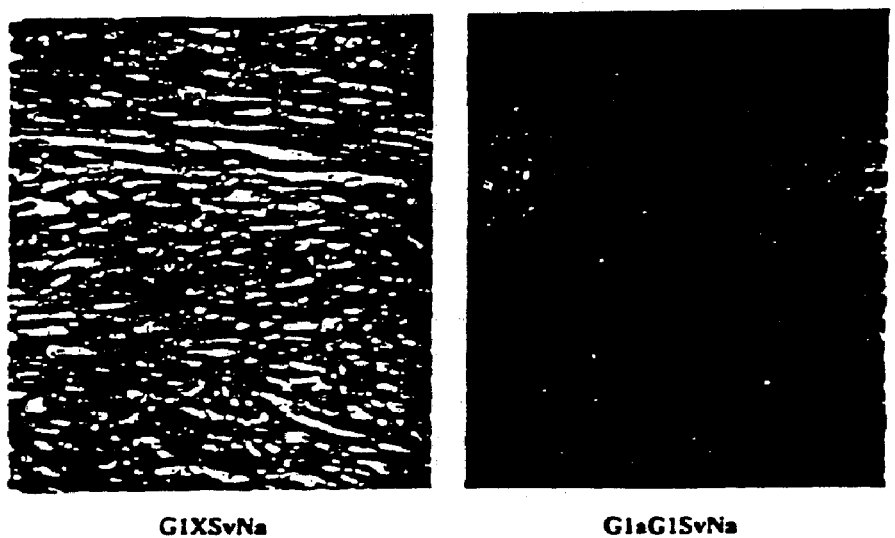
FIG. 13B: Hematoxylin-eosin stain of formalin-fixed tumor sections one week following treatment with retroviral vectors bearing antisense cyclin G1 (G1aG1SvNa) or the control vector (G1XSvNa). 40× magnification.

The mice treated with the antisense cyclin G1 vector showed grossly smaller tumors than control mice. FIG. 13A shows representative antisense cyclin G1 versus control vector-treated mice while FIG. 13B shows the histopathologic characteristics of formalin-fixed and H&E stained VX2 tumor sections, harvested at 21 days (one week after completion of treatment). The sections of tumors that were treated with the control vector showed areas of increased cell density with anaplastic spindle-shaped cells and numerous mitotic figures. In contrast, the sections of tumors that were treated with the antisense cyclin G1 vector showed areas of decreased cell density with less mitotic figures and notable mononuclear cell infiltration. However, residual tumor cells were noted in sections of tumor that received the antisense cyclin G1 vector, indicating that a population of tumor cells were not effectively transduced. Taken together, the retroviral vector expressing antisense cyclin G1 appears to exhibit antitumor effects in vivo in this tumor model of undifferentiated carcinoma.

Discussion

Cancer is a leading target for gene therapy because patients with cancer, particularly those with metastatic disease, often have few or no treatment options, and would be eligible for experimental therapies. The retroviral vector delivery system has been used in 76 of the 106 human trials approved. This vector system utilizes a replication incompetent mouse retrovirus, and thus far, its use, both ex vivo and in vivo, has not caused any major side effects.

Other gene therapy strategies include 1) enhancement of the immune response by injection of tumor vaccines containing transduced irradiated tumor cells expressing cytokines, MHC Class 1 or B7 genes, 2) enforced expression of tumor suppressor genes, 3) knock-out of protooncogene overexpression by antisense vectors, and 4) enforced expression of growth factor receptor genes. In recent years, overexpression or amplification of various cell cycle control genes have been reported in various malignant disorders, indicating that antisense knock-out of these overexpressed genes could be used to re-establish control of cell proliferation, induce cytostasis, inhibit tumor growth and decrease tumor burden.

These concepts arise from initial studies of the budding yeast *S. cerevisiae* wherein extracellular signals that modulate the growth and differentiation act via regulation of a G1 control point termed START (Hartwell, *Science*, Vol. 183, pgs. 46-51 (1974); Cross et al., *Ann. Rev. Cell Biol.*, Vol. 5, pgs. 341-395 (1989)), which is loosely analogous to the G1 restriction point (R point) observed in animal cells in culture (Pardee, *Science*, Vol. 246, pgs. 603-608 (1989)). Therefore, the finding that G1 cyclins (Clns) in *S. cerevisiae*, in association with a Cdk subunit (Cdc28), were required for cells to pass START led to the hypothesis that G1 specific cyclins may indeed function as upstream components of the mammalian S phase Promoting Factor (Draetta, *Trends Biochem. Sci.*, Vol. 15, pgs. 378-383 (1990); Reed, *Trends in Genetics*, Vol. 7, pgs. 95-99 (1991)). Screening of human cDNA libraries for genes that could serve to rescue Cln-deficient yeast cells led to the identification and molecular cloning of three novel families of human G1 cyclins (cyclins C, D, and E: Lew et al., *Cell*, Vol. 66, pgs. 1197-1206 (1991); Koff et al., *Cell*, Vol. 66, pgs. 1217-1228 (1991); Xiong et al., *Cell*, Vol. 65, pgs. 691-699 (1991); Sherr, *Cell*, Vol. 73, pgs. 1059-1065 (1993)). Subsequent studies have mapped the PRAD1/Cyclin D1 gene to chromosome 11q13, implicating cyclin D1 as the BCL-1 oncogene that is translocated and overexpressed in B cell neoplasms (Rosenberg et al., *Proc. Nat. Acad. Sci.*, Vol. 88, pg. 9638 (1991); Withers et al., *Mol. Cell. Biol.*, Vol. 11, pg. 4846 (1991)) and as the 11q13 oncogene that is amplified and overexpresssed in squamous cell, breast, esophageal, and bladder cancers (Lammie et al., *Oncogene*, Vol. 6, pg. 439 (1991); Jiang et al., *Cancer Res.*, Vol. 52, pg. 2980 (1992); Motokura et al., *Curr. Opin. Genet. Dev.*, Vol. 3, pg. 5 (1993)). Genetic amplification, increased expression, and altered metabolism of cyclin E has also been observed in human cancer cells (Buckley et al., *Oncogene*, Vol. 8, pg. 2127 (1993); Keyomarsi et al., *Cancer. Res.*, Vol. 54, pg. 380 (1994)). More recently, a human G-type cyclin, a G1 cyclin that was markedly overexpressed in a subset of osteosarcoma cells was isolated (Wu et al., 1994). Taken together, these findings affirm that constitutive, ectopic, or deregulated expression of G1 cyclins, which normally link signal transduction pathways to the enzymatic machinery of the cell cycle (Hunter and Pines, *Cell*, Vol. 66, pgs. 1071-1074 (1991); Sherr, (1993)), may play an important role in neoplastic transformation and tumorigenesis (Hunter and Pines, *Cell*, Vol. 79, pgs. 573-382 (1994)), and could be used as strategic checkpoints for development of novel gene therapy approaches to cancer and hyperproliferative disorders.

In this study, the safety and efficacy of an antisense cyclin G1 retroviral vector supernatant as a potential gene therapy approach to cancer was tested. A wide variety of cancer cells showed sensitivity to antisense knockout cyclin G1 in comparison to wild-type p53. The proliferation of some non-cancerous cells also was inhibited by the antisense cyclin G1 vector, suggesting its potential utility in the management of non-malignant fibroproliferative disorders as well. Hence, various cell types showed differential sensitivity to cell cycle modulators. The antisense cyclin G1 vector had profound effects on the cell cycle kinetics of both carcinomatous and sarcomatous tumor cells, with a net effect of decreased DNA synthesis, as evidenced by a reduction of cells in S phase. These data suggest that the mechanism of cytostasis in these transduced cells accompanies a G1 phase cell cycle block. Upon selection of transduced cells with G418, only 5% of the VX2 cells were eliminated, indicating that the vast majority of cells bearing antisense cyclin G1 and wild type p53 had undergone cell death, presumably via apoptosis.

Finally, in vivo tumor growth was inhibited dramatically by successive intratumoral injection of a concentrated antisense cyclin G1 retroviral vector supernatant. In contrast, tumor growth was not arrested in the mice treated with the control vector. Histologic examination of the tumors one week after cessation of treatment showed areas of increased cell density with anaplastic spindle-shaped cells and numerous mitotic figures in control vector-treated tumors. In contrast, the sections of tumors that were treated with the antisense cyclin G1 vector showed areas of decreased cell density with less mitotic figures and notable mononuclear cell infiltration. Taken together, these findings represent the first demonstration of in vivo antitumor activity of a retroviral vector expressing antisense cyclin G1 in a model of undifferentiated carcinoma.

Example 3

Inhibition of In Vivo Tumor Growth by a Retroviral Vector Bearing Antisense Cyclin G1 in Athymic Nude Mice Osteosarcoma tumors were grown over two weeks in athymic nude mice by subcutaneous injection of $1 \times 10^7$ MNNG/HOS cells. When the tumors reached 100 mm$^3$ in size, 100 µl of concentrated retroviral vector supernatant (G1XSvNa control vector, bearing only the neo$^R$ gene, or G1aG1SvNa, bearing the antisense cyclin G1 gene: vector titers: each $1 \times 10^8$ cfu/ml) were injected intratumorally every day for 10 days.

The tumor volume was measured at intervals of 0, 4, 6, 8, 10, and 12 days after vector injection. FIG. 14 shows the tumor volume at each of the above-mentioned intervals. As shown in FIG. 14, the antisense cyclin G1 vector-treated mouse has a smaller tumor than the control vector-treated mouse.

Hematoxylin and eosin staining of formalin-fixed MNNG/HOS tumor sections for two days following the treatment with the retroviral vectors bearing the antisense cyclin G1 gene (G1aG1SvNa) or the control vector (G1XSvNa) shows decreased mitotic index (1% for antisense cyclin G1-treated tumors versus 3.5% for control vector-treated tumors), and increased stroma formation.

FACS analysis of PI-stained nuclei obtained from MNNG/HOS tumors showed a dramatic decrease in the number of aneuploid cells in the antisense cyclin G1 vector-treated tumors (2%) compared with that in control vector treated tumors (45%). Further, the diploid population of cells from the antisense cyclin G1 vector-treated tumors showed a 77% accumulation of cells in G1 phase versus 49% in G1XSvNa control vector-treated tumors, and a significant decrease in the number of cells in S phase (15% versus 25%), which suggests that the mechanism of cytostasis in the transduced tumors was accompanied by a G1 phase cell cycle block.

Example 4

Materials and Methods

Retroviral Vectors, Vector Supernatants and Producer Cell Lines.

The cDNA sequence encoding human cyclin G1 (Accession #X77794) is as originally described by Wu et al., 1994. The experimental vector bearing the antisense cyclin G1 cDNA (Wu, et al., 1994) was packaged in PA317 cells and grown to high titer clones (vector titer: $1 \times 10^6$ cfu/ml each). The β-galactosidase and p53 expression vectors were provided kindly as high titer PA317 packaging cell clones (titers: $5 \times 10^5$ and $2 \times 10^6$ colony-forming units, cfu/ml for β-galactosidase and p53 vectors respectively) by Genetic Therapy, Inc. (Gaithersburg, Md.). The vectors are referred to as G1nBg5vNa (described in PCT Application Nos. WO95/19427, published Jul. 20, 1995 and WO96/22212, published Jul. 25, 1996), G1pS3SvNa.7, and G1aG1SvNa to indicate the order of promoters and coding regions contained in each vector (G1, Moloney murine leukemia virus long terminal repeat (LTR) sequences; Bg, β-galactosidase gene; p53, p53 tumor suppressor gene; aG1, antisense human cyclin G1; Sv, SV40 early region enhancer/promoter; and Na, neo$^r$ gene). The retroviral vector supernatants were concentrated further to a titer of $1 \times 10^8$ cfu/ml by low speed centrifugation. The vector backbone, G1XSvNa, containing only the SV40 promoter-driven neo$^r$ gene was used as a control for the effects of transduction and G418 selection.

Cells, Cell Culture Conditions, and Transduction with Retroviral Vectors.

Rat aortic smooth muscle (A 10) cells were obtained from ATCC (Cat. #CRL1476) and maintained as monolayers at a plating density of $2.5 \times 10^4$ cells per well, in DMEM supplemented with 10% fetal bovine serum (FBS; D10). After overnight attachment, the cells were exposed to 1 ml of the respective retroviral vector in the presence of Polybrene (8 µg/ml) for 2 hours, with periodic rocking, after which 1 ml of fresh D10 was added to each well. Forty-eight hours after transduction with the β-galactosidase vector, gene transfer efficiency was measured by determining the percentage of β-galactosidase positive cells, upon exposure to X-gal (β-galactosidase) staining as described in Lal, et al., *J. Histochem. Cytochem.*, Vol. 42, pgs. 953-956 (1994), and visualization by light microscopy.

Analysis of Cell Proliferation, DNA Synthesis, Cyclin G1 Protein Expression and Apoptosis To assess the cytostatic effects of retroviral vectors bearing cell cycle modulators, the SMC that were transduced with control vectors or vectors expressing antisense cyclin G1 (or p53) gene(s) were evaluated for their proliferative potential by counting the number of viable cells in each culture at serial intervals after transduction. Values shown represent the mean of triplicate±standard deviation (S.D.). The effect of cell cycle modulators on DNA synthesis was monitored by the incorporation of $^3$H-thymidine into DNA as described in Gordon, et al., *Proc. Nat. Acad. Sci.*, Vol. 93, pgs. 2174-2179 (1996). Briefly, 24 hrs. after transduction with the antisense cyclin G1 or control retroviral vector, the cell cultures were exposed to $^3$H-thymidine (1 µCi per well; specific activity, 6.7 Ci/mmol; 1 Ci=37 GBq; New England Nuclear) for 2 hrs. The cells were then placed on ice, rinsed twice with cold phosphate-buffered saline (PBS), and then rinsed three times with ice-cold 5% trichloroacetic acid (TCA). The final TCA rinse was removed and the TCA-precipitated material was solubilized with 0.2 ml of 1M sodium hydroxide followed by neutralization with an equal volume of 1M acetic acid. $^3$H-thymidine incorporation into cellular macromolecules was measured by liquid scintillation counting and expressed as radioactivity units in dpm/well. The significance of differences between untreated and vector-treated groups was determined by analysis of variance (ANOVA).

Western Blot analysis of cyclin expression was performed as described in Wu, et al., *Int. J. Oncol.*, Vol. 3, pgs. 859-867 (1993) and Colton, *Statistics in Medicine*, pg. 99, Little, Brown & Co., (1974), using a polyclonal antipeptide antibody recognizing the C-terminal 18 amino acids of human cyclin G1 (Wu, et al., 1994). The occurrence of apoptosis in transduced cell cultures was evaluated with the Apoptag Plus in situ detection kit (Oncor), which detects nascent 3'-OH DNA ends generated by endonuclease-mediated DNA fragmentation utilizing enzymatic (terminal deoxynucleotidyl transferase; TdT) addition of digoxigenin-labeled nucleotides followed by immunocytochemical detection of the modified DNA fragments (Skotzko, et al., *Cancer Res.*, Vol. 55, pgs. 5493-5498 (1995)).

Retrovirus-Mediated Transfer of the Antisense Cyclin G1 Gene in a Rat Carotid Injury Model of Vascular Restenosis.

Under general anesthesia (ketamine, 10 mg/kg; rompun, 5 mg/kg), in accordance with a protocol approved by the USC Institution Animal Care and Use Committee (IACUC), a 2F Intimax arterial embolectomy catheter (Applied Medical Resources Corp., Laguna Hills Calif.) was used to denude the carotid artery endothelium of Wistar rats (each weighing 400-500 gm). The catheter was inserted into the external carotid artery which was ligated distally, and passed into the common carotid artery. The balloon was inflated to a volume of 10 µl and passed 3 times along the length of the common carotid artery. After balloon injury, the embolectomy catheter was removed and the internal carotid artery was ligated transiently just distal to the bifurcation. The distal half of the injured segment was likewise transiently ligated, and then exposed to the retroviral vectors for 15 minutes. Each group of animals received an infusion of 100 µl of concentrated high titer antisense cyclin G1 vector (n=7) or a control vector bearing only the $neo^r$ gene (n=4), after which the rats were allowed to recover, and fed a regular mouse/rat diet and water ad libitum. For purposes of analgesia, the animals were given buprenex, 0.2 mg/kg s.c. every 12 hours for 72 hours post-operatively. The rats were sacrificed 2 weeks after induction of vascular injury by an overdose of sodium pentobarbital (120 mg/kg IM), and formalin-fixed sections of both injured and non-injured contralateral carotid arteries were stained with hematoxylin-eosin, Siris red-Verhoeffs elastin stain. Histologic sections were examined by light microscopy, and morphometric evaluation of the neointima versus media surface areas was conducted using a digitizing system; the extent of intimal hyperplasia following vascular injury is expressed as neointima to media ratios. The significance of differences between the neointima to media ratios of non-treated and vector-treated vessels was determined by paired t-test (Colton, 1974).

Results

Transduction of Aortic SMC with Retroviral Vectors Bearing Cell Cycle Control Genes.

Figure 15A:
FIG. 15: (A) Aortic smooth muscle cells expressing nuclear-targeted β-galactosidase (cells with blue nuclei) following transduction with the G1nBgSvNa vector; (B) Cytostatic and cytocidal effects of antisense cyclin G1 and wild type p53 in transduced aortic SMC. Cell densities were measured by direct cell counting in cultures of aortic SMC harvested at serial intervals after transduction with retroviral vectors bearing antisense G1 (G1aG1SvNa) and wild type p53 (G1pS5SvNa) as well as the control vector (G1XSvNa); (C) $^3$H-thymidine incorporation in cultured aortic SMC after transduction with retroviral vectors (n=3 each group). Radioactivity is expressed as dpm per well. Results are expressed as arithmetic mean±1 standard deviation.
Figure 15B:
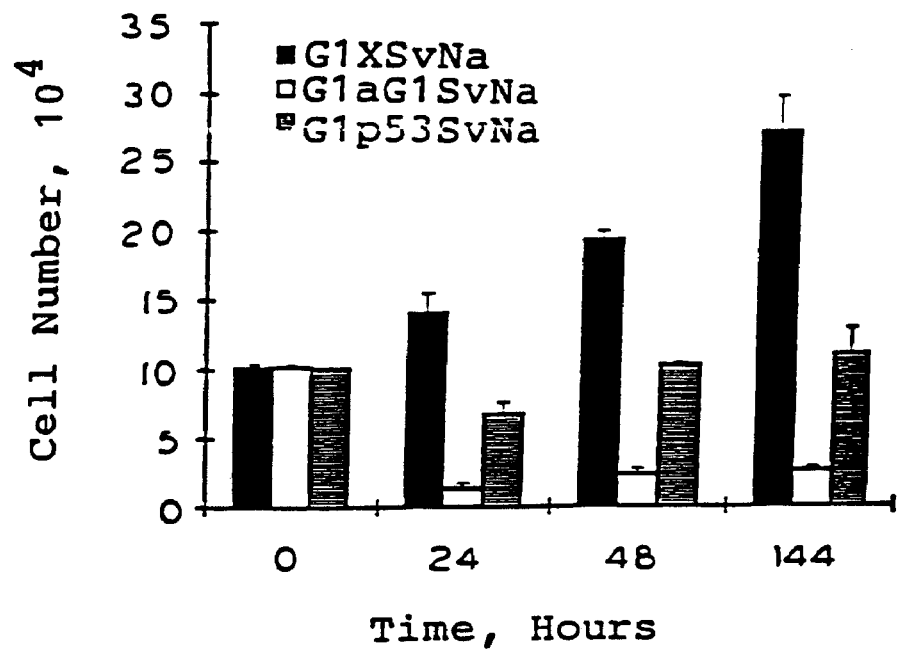
Figure 15C:
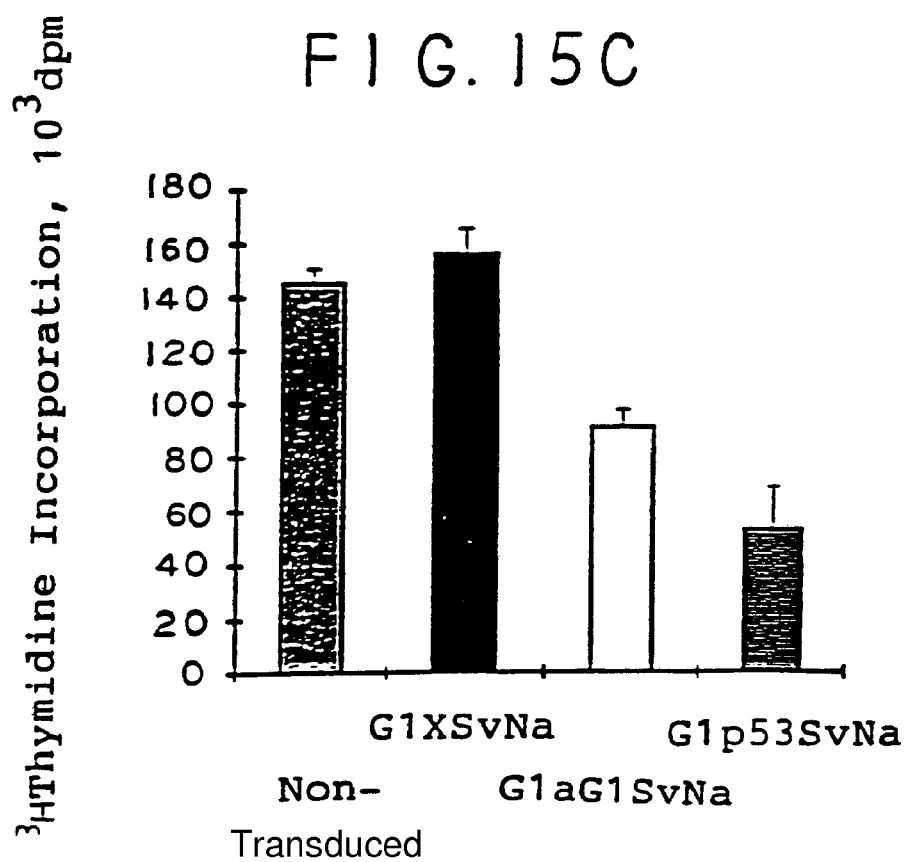

Using a nuclear-targeted β-galactosidase vector (G1nBgSvNa), the apparent transduction efficiency of rat (A10) aortic SMC was about 45% (FIG. 15A), which was similar to murine NIH3T3 cells, and somewhat greater than normal human fibroblasts or scar-derived (keloid) fibroblasts in which transduction efficiencies of 20% and 30%, respectively, were observed. Transduction of aortic SMC with vectors bearing antisense cyclin G1 (aG1) showed a marked decrease in the number of viable cells observed at 24 to 144 hours post-transduction, when compared to transduced cultures containing the empty (control) vector (FIG. 15B). Western Blot analysis confirmed down-regulation of cyclin G1 protein expression in aortic SMC transduced with antisense cyclin G1 when compared to the control vector (not shown). Proliferation of A 10 cells was also inhibited by retroviral mediated overexpression of the p53 tumor suppressor gene in sense orientation. Both antisense cyclin G1 and p53 vectors inhibited cell cycle progression, as determined by the incorporation of $^3$H-thymidine (p<0.001 for both aG1 and p53; FIG. 15C).

Antisense Cyclin G1 Induces Degeneration, Multicellular Syncytia Formation, and Apoptosis in Aortic SMC.

The photomicrographs shown in FIG. 16 display the morphological appearance of aortic SMC observed by light microscopy at 24 hours after transduction with control and antisense cyclin G1 retroviral vectors. As shown in FIG. 16A, the cells transduced with the control vector showed no significant morphologic changes. In contrast, a significant decrease in cell density was observed in cultures transduced with vectors bearing antisense cyclin G1, associated with overt degenerative changes, increased multinuclear syncytium formation, and cytolysis (FIGS. 16B, 16C, 16D). Remarkably, the proportion of cells involved in the syncytia far exceeded the transduction efficiency as determined by the transduction and expression of β-galactosidase. Syncytium formation occurred in A10 cultures transduced with the antisense cyclin G1 vector supernatants derived from three different high titer clones, as well as the p53 vector to some extent, but not in the control (G1XSvNa) or β-galactosidase vectors. To further investigate the mechanisms of cell death, a molecular and immunocytochemical approach was employed to detect the endonuclease-mediated DNA cleavage fragments that are characteristic of apoptosis. As shown in FIGS. 16E and 16F, no evidence of apoptosis was observed in cells transduced with the control vector (FIG. 16E); however, a number of apoptotic cells were observed in the antisense cyclin G1 vector-transduced cultures (FIG. 16F). These results indicate that the cytocidal effects of the antisense cyclin G1 vector in A10 aortic SMC result in part from apoptosis, cell degeneration, and aberrant syncytium formation.

Evidence for a Cytocidal "Bystander" Effect in Aortic SMC Cultures Transduced with Antisense Cyclin G1 Retroviral Vectors.

To confirm that non-transduced cells were incorporated into the multicellular syncytia found in antisense cyclin G1-transduced cultures, we loaded non-transduced A10 cells with a fluorescent marker and overlaid the marked cells on previously transduced cultures two hours after washout of the vector supernatant. The incorporation of non-transduced, flourescently-labeled A10 smooth muscle cells into multinuclear syncytia clearly was evident when these marked cells were overlaid onto previously transduced A10 cultures (FIGS. 17A and 17B, low magnification; 17C and 17D, high magnification; 17A and 17C, phase contrast; 17B and 17D, UV light). A representative multinuclear syncytium incorporating cells containing the flourescent label is identified by the arrow. Twenty-four hours after co-culture with non-transduced, fluorescently-labelled aortic SMC, a considerable number of the multinucleated syncytia were also labelled with the fluorescent dye, indicating that cell fusion between the transduced and non-transduced cells had occurred. This finding provides additional evidence of a novel cytocidal "bystander effect" distinguishable from the classic "bystander effect" induced by the Herpes Simplex Virus thymidine kinase/ganciclovir system and mediated by gap junctions present in susceptible cells.

Figure 17E:
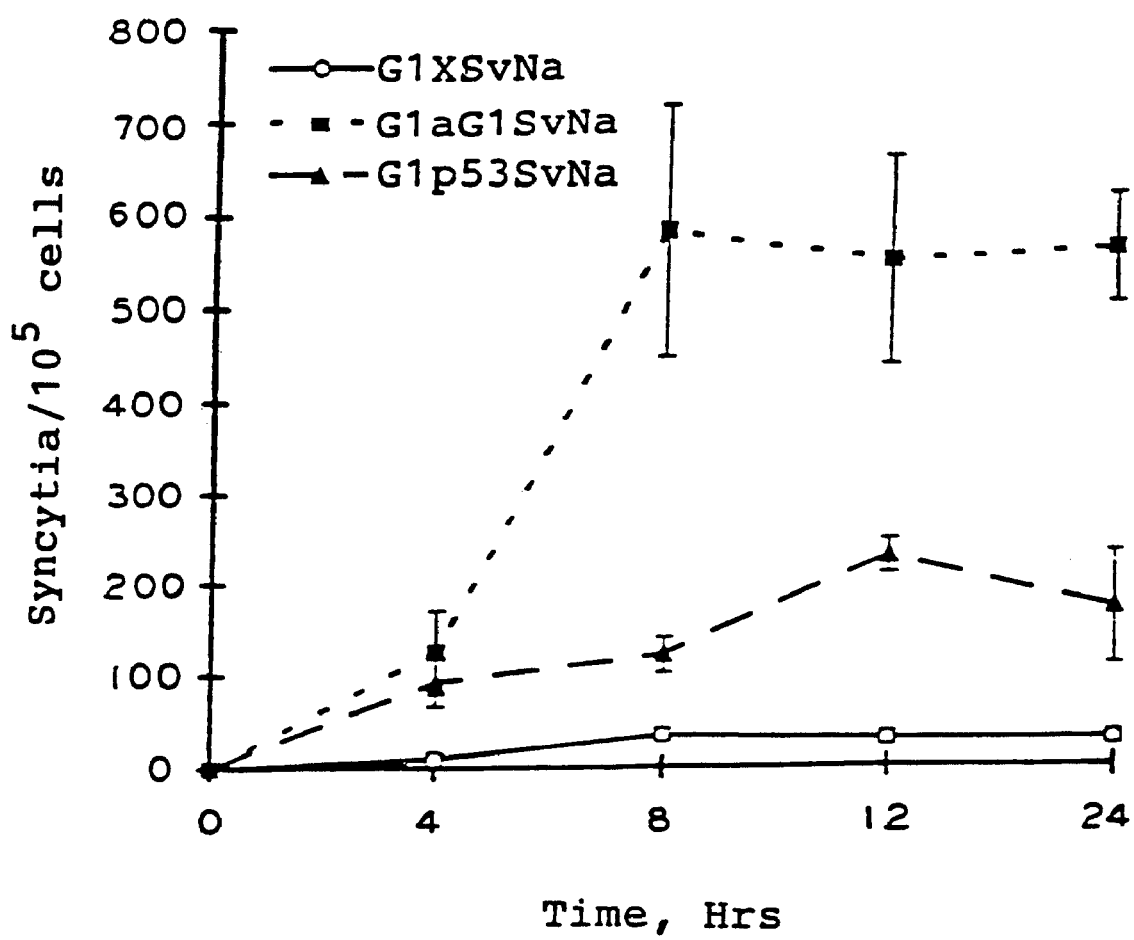
FIG. 17: Cytocidal "bystander" effect in antisense cyclin G1 vector-transduced aortic SMC. Incorporation of non-transduced, fluorescently labeled aortic SMC into multicellular syncytia when overlaid onto an SMC culture previously transduced with an antisense cyclin G1 vector. A and B, low magnification; C and D, high magnification; A and C, phase contrast; B and D, UV light. A representative multinuclear syncytium incorporating cells containing the fluorescent label is identified by the arrow. (E) Quantification of syncytia formation over time in vascular SMC transduced with retroviral vectors: G1XSvNa, control vector; G1aG1SvNa, vector bearing antisense cyclin G1 gene; G1p53SvNa, vector bearing wild type p53.

The phenomenology of cell fusion was followed over time (FIG. 17E, revealing a significant increase in the number of syncytia that increased over 4-8 hours in aortic SMC that were transduced with the antisense cyclin G1 vector (G1aG1SvNa), when compared to the cells transduced with the control vector (G1XSvNa; p<0.001). An appreciable degree of syncytium formation also was noted in cells that were transduced with the wild-type p53 vector (G1p53SvNa) which also produced marked cytostasis in A10 cells. However, the number of syncitia observed in p53 transduced cells was significantly less than that observed in aG1 transduced cells at 8, 12 and 24 hours (p<0.001).

The Antisense Cyclin G1 Vector Inhibits Proliferation and Migration of Aortic Smooth Muscle Cells in an In Vitro "Tissue" Injury Model.

Figure 18A:
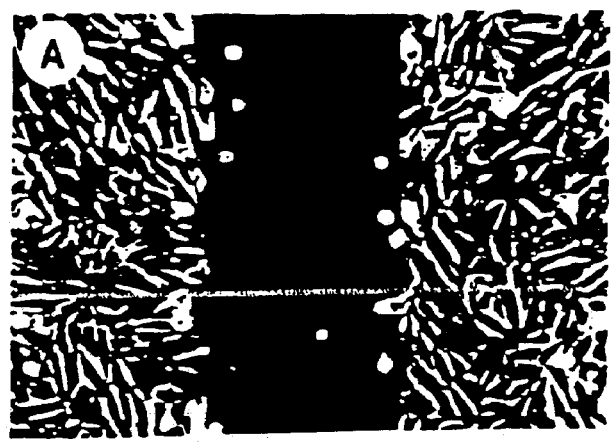
FIG. 18: (A) High density cultures of aortic SMC scraped with a 200 µl pipet tip to create a 1 mm track devoid of cells, (B) The appearance of the "wound" margin immediately upon scraping and washing to remove detached cells, (C) Aortic SMC expressing nuclear targeted β-galactosidase along the margins of the track, (D) Proliferation and migration of G1XSvNa control vector-transduced aortic SMC into the track at 24 hrs after injury, (E) Apoptotic and degenerative changes in G1aG1SvNa vector-transduced aortic SMC with marked syncytia formation.
Figure 18B:
Figure 18C:
Figure 18D:
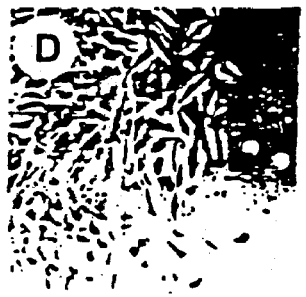
Figure 18E:

High density (confluent) monolayer cultures of A10 SMC exhibiting contact inhibition of cell growth can be stimulated to proliferate along a track of cell/tissue disturbance exhibiting a characteristic "wound healing" response over a period of 7 days. FIG. 11A shows high density cultures of aortic SMC scraped with a 200 μl pipet tip to create a 1 mm track devoid of cells. FIG. 18B shows the appearance of the "wound" margin immediately upon scraping and washing to remove the detached cells. As shown in FIG. 18C, subsequent transduction of the cell cultures (at t=24 hours) with a nuclear-targeted β-galactosidase vector was greatest at the margins of the "wound", an area of activated SMC proliferation. FIG. 18D shows proliferation and migration of aortic SMC into the wound track at t=24 hours after injury. In contrast, apoptotic and other degenerative changes were observed in the SMC that were transduced with the antisense cyclin G1 vector (FIG. 18E). Notably, these degenerative changes were marked by multicellular syncytia formation that was not observed in either the control or β-galactosidase vector. Further, cell proliferation and overt cell migration into the wound track was reduced markedly in the antisense cyclin G1-transduced cell cultures, evidenced by delayed closure of the wound track (about 7 days) compared to the control vector-treated cultures (about 3 days).

Inhibition of Neointima Formation In Vivo by Infusion of High Titer Antisense Cyclin G1 Vector Supernatant.

Figure 19A:
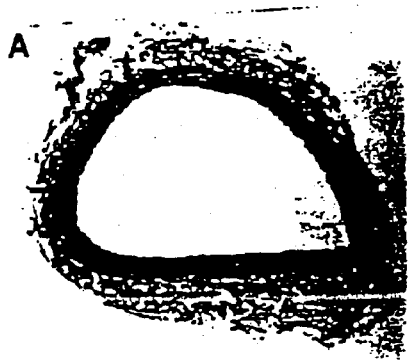
FIG. 19: Test of efficacy of an antisense cyclin G1 vector in the rat carotid artery injury model of restenosis. The elastin layer of the tunica media is identified (in A-D) by Verhoeff's stain. The neointima, comprised of proliferating smooth muscle cells (reddish yellow staining cells), is identified by Siris red stain. A and C=non-treated arterial segments; B and D=antisense cyclin G1 vector-treated arterial segments. E and F=higher magnification of non-treated and aG1-treated arterial segments, respectively; G=Analysis of neointima to media ratios of non-treated (NT), control (GIX) and antisense cyclin G1 (aG1)-treated arterial segments are represented as vertical bars.
Figure 19B:
Figure 19C:
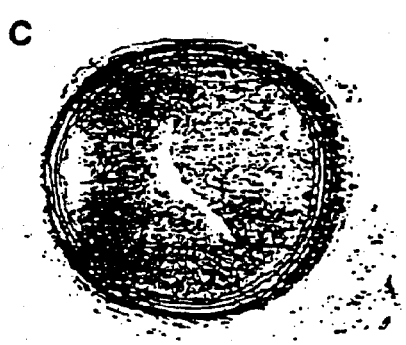
Figure 19D:
Figure 19E:
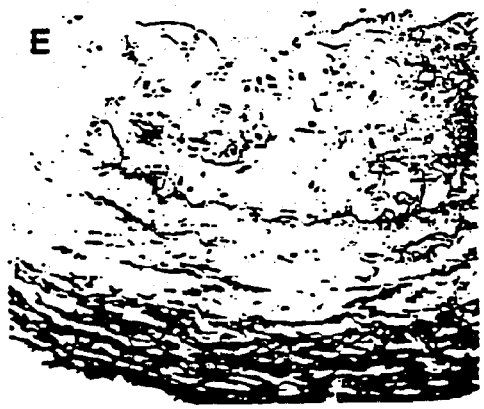
Figure 19F:
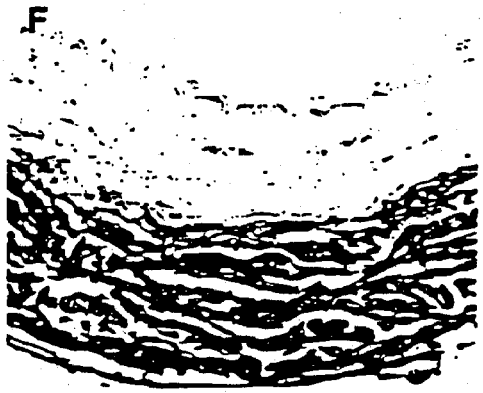
Figure 19G:
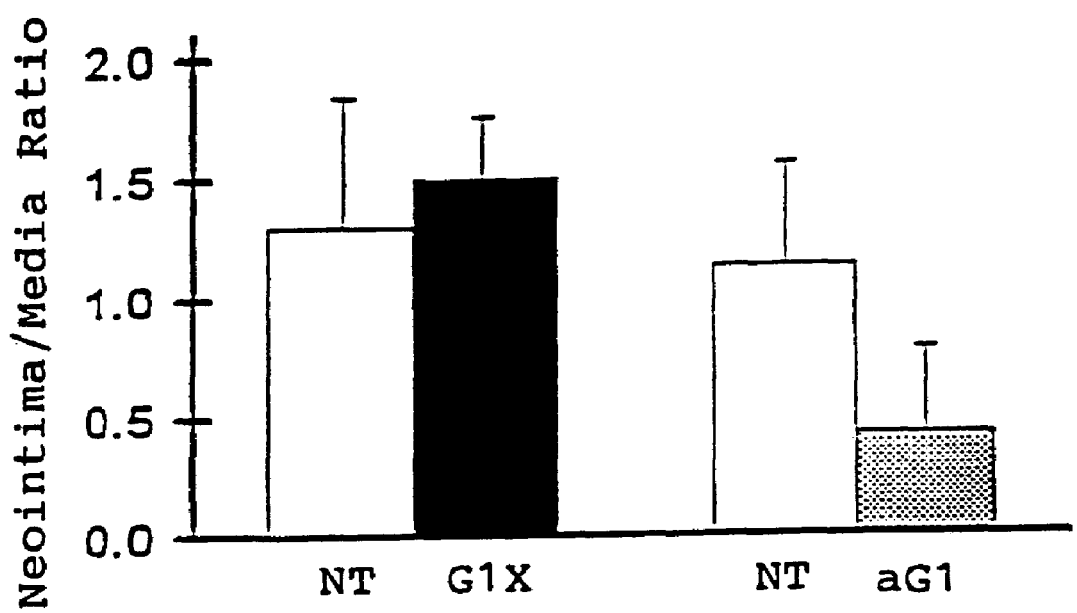

Previous studies demonstrated direct transfer of recombinant marker genes into the arterial wall by retroviral vectors with viral titers of $10^4$-$10^6$ particles/ml (Nabel, et al., *Science*, Vol. 249, pgs. 1285-1288 (1990)), and a number of studies have demonstrated the efficacy of cytostatic gene therapies delivered by other methods in animal models of vascular restenosis. In this study, high titer retroviral vector supernatants (viral titer: $1 \times 10^{84}$ cfu/ml) were generated to test the efficacy of antisense cyclin G1 delivered by highly concentrated retroviral vectors in the rat carotid injury model of restenosis. Histologic examination of stained sections obtained from balloon-injured untreated arteries showed substantial neointima formation at 2 weeks, as evidenced by invasion of the tunica intima by proliferating vascular SMC (FIGS. 19A and 19C). In contrast, injured arterial segments that were treated with high titer antisense cyclin G1 vector supernatants showed a significant reduction in neointima formation (FIGS. 19B and 19D). Morphometric analysis confirmed significant inhibition in neointima formation in injured carotid arteries that were treated with the antisense cyclin G1 retroviral vector (I:M ratio 0.4±S.D. 0.4) compared to the untreated arterial segments (I:M ratio 1.1±0.4; pc 0.001; FIG. 19G). In control studies, there was no difference between the extent of neointima formation in non-treated arterial segments (I:M ratio 1.3±SD 0.5) when compared with high titer vectors containing only the $neo^r$ gene (I:M ratio 1.5±0.2).

Discussion

Clinical trials based on the molecular blockade of identified growth factors and/or growth factor receptors implicated in the pathogenesis of intimal hyperplasia have not proven to be effective vehicles for cytostatic vascular therapy (Faxon, et al., *J. Amer. Coll. Cardiol.*, Vol. 25, pgs. 362-369 (1995)). Thus, it has been suggested that approaches which target intracellular signalling cascades that are shared by many growth regulatory molecules may be more strategic (Gibbons, et al., *Science*, Vol. 272, pgs. 689-693 (1996)). Accordingly, novel gene therapy approaches to inhibit SMC proliferation and neointima formation have focused recently on cell cycle control mechanisms. Indeed, antisense approaches against cell cycle regulatory genes has been shown to be remarkably effective in limiting neointimal hyperplasia in animal models of lesion formation following both bypass surgery (Mann, et al., *Proc. Nat. Acad. Sci.*, Vol. 92, pgs. 4502-4506 (1995)) and balloon angioplasty. A single intraluminal delivery of antisense Cdc2 kinase or Cdk2 kinase produced significant inhibition of neointimal hyperplasia Morishita, et al., *Proc. Nat. Acad. Sci.*, Vol. 90, pgs. 8474-8478 (1993); Morishita, et al., *J. Clin. Invest.*, Vol. 93, pgs. 1458-1464 (1994); Abe, *Biochem. Biophys. Res. Comm.*, Vol. 198, pgs. 16-24 (1994)). An adenoviral vector bearing a nonphosphorylatable, constitutively active form of Rb also was reported to inhibit SMC proliferation and neointima formation following balloon angioplasty (Chang, et al., *Science*, Vol. 267, pgs. 518-522 (1995)). Molecular strategies directed against E2F also have been developed, as the concerted induction of numerous cell cycle regulatory genes is regulated by this transcription factor. Oligonucleotides containing the E2F cis element sequence function as "decoys" that bind E2F within the cell and inhibit neointimal lesion formation in vivo (Morishita, et al., *Proc. Nat. Acad. Sci.*, Vol. 92, pgs. 5855-5859 (1995)). Further support for the concept of cytostatic gene therapy based on the inhibition of cell cycle control enzymes is provided by recent findings that rapamycin, which inhibits the activation of cell division/cycle enzymes (Albers, et al., *Ann. New York Acad. Sci.*, Vol. 696, pgs. 54-62 (1993); Albers, et al., *J. Biol. Chem.*, Vol. 268, pgs. 22825-22829 (1993); Jayaraman, et al., *J. Biol. Chem.*, Vol. 34, pgs. 25385-25388 (1993), also inhibits vascular lesion formation in both rat and porcine models (Gregory, et al., *Transplantation*, Vol. 59, pgs. 655-661 (1995); Marx, et al., *Circ. Res.*, Vol. 76, pgs. 412-417 (1995)).

Cyclin G1 is a member of the so-called G1 family of cyclins which act in concert with cyclin-dependent protein kinases during the G1 phase of the cell cycle (Wu, et al., *Int. J. Oncol.*, Vol. 3, pgs. 859-867 (1993); Sherr, *Cell*, Vol. 79, pgs. 551-555 (1994)). Induced in early G1 and suspected to participate in the molecular mechanisms of cell activation (Wu et al., *Oncol. Reports*, Vol. 1, pgs. 705-711 (1994)), cyclin G1 appears to be a transcriptional target of the p53 tumor suppressor gene (Okamoto, et al., *EMBO J.*, Vol. 13, pgs. 4816-4822 (1994)). Cyclin G1 overexpression was first linked to cancer (Wu, et al., 1994) and, more recently, down-regulation of cyclin G1 expression by retroviral vectors bearing antisense CYCG1 was reported to inhibit the growth and survival of human osteosarcoma (MG-63) cells (Skotzko, et al., 1995).

In this example, the effects of retroviral vectors bearing an antisense cyclin G1 construct on the proliferation of A10 rat aortic smooth muscle cells were examined. Retroviral vectors bearing the antisense cyclin G1 gene, as well as the p53 gene, in sense orientation, inhibited the survival and proliferation of transduced A10 cells in 2-6 day cultures. Cytostasis was associated with decreased DNA synthesis and down-regulation of cyclin G1 in vascular SMC transduced with the antisense cyclin G1 vector as compared to those transduced with the control vector. Morphological examination of the transduced SMC revealed cytolysis, giant syncytia formation, and overt apoptotic changes evidenced by cell shrinkage, nuclear fragmentation, and chromatin condensation observed in both antisense cyclin G1 vector- and p53 vector-transduced A10 cells. However, the number of multinuclear syncytia were found to be significantly higher in the cell cultures treated with the antisense cyclin G1 vector. Pronounced "bystander" effects were noted in A10 cells transduced with the antisense cyclin G1 vector as determined by quantitative cell fusion assays and the fluorescent labeling of non-transduced cells. These findings indicate that the antisense cyclin G1 vector induces a "fusion-promoting factor", possibly a protease or glycosylase, that facilitates cell fusion and syncytia formation, perhaps by augmenting mechanisms related to the fusogenic properties of the MoMuLV envelope protein (Jones, et al., *J. Virol.*, Vol. 67, pgs. 67-74 (1993)).

Figure 16A:
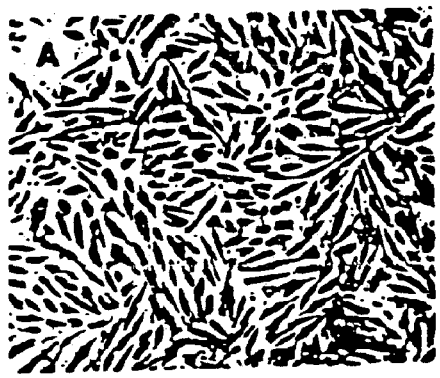
FIG. 16: The morphological appearance of aortic SMC, observed by light microscopy at 24 hrs after transduction with control and antisense cyclin G1 retroviral vectors (A=G1XSvNa control vector; B-D=G1aG1SvNa). Detection of apoptosis in vascular SMC after antisense cyclin G1 retroviral vector transduction; (E) G1XSvNa control vector-transduced cells, (F) G1aG1SvNa antisense cyclin G1 vector-transduced cells. The dark-staining apoptotic bodies are noted both within and out of the syncytial cells.
Figure 16B:
Figure 16C:
Figure 16D:
Figure 16E:
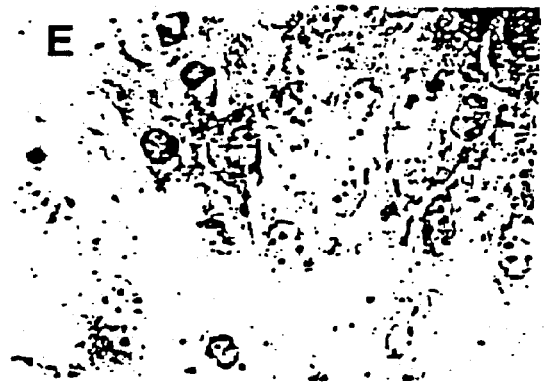
Figure 16F:

Cytostatic gene therapies for restenosis show promise of additional therapeutic consequences in that the inhibition of cell cycle regulatory genes is reported to trigger vascular cell apoptosis (Gibbons, et al., 1996; Laird, et al., *Circulation*, Vol. 93, pgs. 529-536 (1996)). In mitotically activated SMC, as in osteosarcoma cells (Skotzko, et al., 1995), the cytotoxicity of the cyclin G1 blockade is attributable, at least in part, to the activation of an apoptotic pathway (FIG. 16F). Furthermore, the induction of cell cycle arrest in some circumstances also appears to inhibit SMC migration and extracellular matrix production (Biro, et al., *Proc. Nat. Acad. Sci.*, Vol. 90, pgs. 654-658 (1993)). In the in vitro "tissue injury" model, both the proliferation and migration of A10 cells that were transduced with the antisense cyclin G1 vector were inhibited in the area of cell injury (FIG. 18E). Taken together with the observations of marked cytotoxicity, cell cycle blockade, and multicellular syncytia formation, these findings lend additional support for the concept that cyclin G1 may represent a strategic locus for therapeutic intervention in the management of proliferative disorders.

Once a potential therapeutic gene has been identified, the challenge remains to deliver the gene transfer vector efficiently to the appropriate physiologic site. In the case of balloon angioplasty, both the denudation of the endothelial lining and the mitogenic activation of neighboring SMC provide favorable conditions for the delivery of retroviral vectors, as the therapeutic genes delivered by retroviral vectors are expressed preferentially in mitotically active cells. In the present study, very high titer supernatants ($10^8$ cfu/ml) were generated to enhance the transduction efficiency of vascular SMC, and hence, the efficacy of retroviral vectors in this experimental model of restenosis. Indeed, the in vitro studies of retroviral vector-mediated gene delivery in embryonic A10 SMC, may be particularly relevant to the physiology of restenosis, for numerous reports have indicated that embryonic and neointimal SMC exhibit similar responses to mitogenic signals (Schwartz, et al., *The Vascular Smooth Muscle Cell*, Schwartz, et al., eds. pg. 81-139, Academic Press, Inc., New York (1995)). This study in the rat carotid artery injury model of restenosis demonstrates the efficacy of this approach: Sections of balloon-injured carotid arteries that were treated with an infusion of highly concentrated ($10^8$ cfu/ml) antisense cyclin G1 retroviral vector supernatant showed a significant reduction in neointima formation. Taken together, these data support the utility of retroviral vectors bearing cyclin G1, alone or in combination with p53 or the now-classic Herpes Simplex Virus thymidine kinase/GCV approach, in the development of novel gene therapy strategies to combat vascular restenosis.

The disclosures of all patents, publications, (including published patent applications), database accession numbers, and depository accession numbers referenced in this specification are specifically incorporated herein by reference in their entirety to the same extent as if each such individual patent, publication, database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A method of inhibiting growth of a sarcoma and/or carcinoma in a host comprising:
administering to the host by intratumoral injection an expression vehicle encoding an antisense polynucleotide which is complementary to at least a portion of a polynucleotide encoding cyclin G1 protein and binds to a polynucleotide encoding cyclin G1 protein to prevent expression of the polynucleotide encoding cyclin G1 protein.

2. The method of claim 1 wherein said antisense polynucleotide is administered to said host by transducing tumor cells of said host with an expression vehicle including a polynucleotide encoding said antisense polynucleotide.

3. The method of claim 1 wherein said expression vehicle is a retroviral vector.

4. The method of claim 1 wherein said sarcoma is osteogenic sarcoma.

5. The method of claim 1 wherein said sarcoma is Ewing's sarcoma.

6. The method of claim 1, wherein the antisense polynucleotide is complementary to at least a portion of a polynucleotide encoded by SEQ ID NO:1.

7. The method of claim 1, wherein said expression vector is an adenoviral vector.

* * * * *